US008471107B2

(12) United States Patent
Schillinger et al.

(10) Patent No.: US 8,471,107 B2
(45) Date of Patent: Jun. 25, 2013

(54) SOYBEANS HAVING HIGH GERMINATION RATES AND ULTRA-LOW RAFFINOSE AND STACHYOSE CONTENT

(75) Inventors: John A. Schillinger, Cumming, IA (US); Emily C. Dierking, Columbia, MO (US); Kristin D. Bilyeu, Columbia, MO (US)

(73) Assignees: Schillinger Genetics, Inc., West Des Moines, IA (US); The United States of America as Represented by the Secretary of Agriculture, Washington, DC (US)

( * ) Notice: Subject to any disclaimer, the term of this patent is extended or adjusted under 35 U.S.C. 154(b) by 46 days.

(21) Appl. No.: 12/762,097

(22) Filed: Apr. 16, 2010

(65) Prior Publication Data

US 2011/0003045 A1 Jan. 6, 2011

Related U.S. Application Data

(60) Provisional application No. 61/170,048, filed on Apr. 16, 2009.

(51) Int. Cl.
*A01H 5/00* (2006.01)
*A01H 5/10* (2006.01)
*C12N 15/29* (2006.01)
*C12N 15/82* (2006.01)

(52) U.S. Cl.
USPC ........ 800/312; 435/320.1; 536/23.6; 800/284

(58) Field of Classification Search
None
See application file for complete search history.

(56) References Cited

U.S. PATENT DOCUMENTS

| 5,304,719 A | 4/1994 | Segebart |
| 5,367,109 A | 11/1994 | Segebart |
| 5,523,520 A | 6/1996 | Hunsperger et al. |
| 5,710,365 A | 1/1998 | Kerr et al. |
| 5,850,009 A | 12/1998 | Kevern |
| 5,968,830 A | 10/1999 | Dan et al. |

(Continued)

FOREIGN PATENT DOCUMENTS

| EP | 10250790.2 | 4/2010 |
| WO | WO 00/24915 | * 5/2000 |

OTHER PUBLICATIONS

Neus et al 2005, Crop Science 45: 589-592.*
Dierking et al (2009, J. Plant Physiology 166(12): 1329-1335).*

(Continued)

*Primary Examiner* — David H Kruse
(74) *Attorney, Agent, or Firm* — Barbara Campbell; Cochran Freund & Young LLC

(57) ABSTRACT

Soybean seeds having an ultra-low raffinose and stachyose phenotype. Also disclosed is a mutant allele of soybean designated SG-ULRFO which results in an ultra-low raffinose and stachyose phenotype. The present invention also relates to a soybean seed, a soybean plant and parts of a soybean plant and a soybean hybrid which comprises the mutant allele. Also disclosed are ultra-low raffinose and stachyose soybean seeds having unexpectedly increased germination rates when compared with soybean lines not having a low raffinose and stachyose seed content. Also disclosed are mutant RS3 and RS4 genes with polymorphisms which contribute to the ultra-low raffinose and stachyose phenotype as described in the present invention. The present invention also relates for method of using the soybean seeds and plants of the present invention, to plants parts derived from the present invention, to methods of producing transgenic plants using the plants and seeds of the present invention.

8 Claims, 3 Drawing Sheets

U.S. PATENT DOCUMENTS

| | | | |
|---|---|---|---|
| 6,147,193 | A | 11/2000 | Kerr et al. |
| 6,967,262 | B2 | 11/2005 | Allen et al. |
| 2003/0074685 | A1 | 4/2003 | Hitz et al. |
| 2004/0128713 | A1 | 7/2004 | Hitz et al. |
| 2005/0278807 | A1 | 12/2005 | Allen et al. |
| 2008/0199591 | A1 | 8/2008 | Maroof et al. |
| 2010/0043098 | A1 | 2/2010 | Allen et al. |
| 2010/0077510 | A1 | 3/2010 | Stoop et al. |

OTHER PUBLICATIONS

U.S. Appl. No. 61/170,048, filed Apr. 16, 2009, Schillinger, J.
Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. App. Genet. 101:323-326.
Willmot, et al., 1989. Genetic analysis of brown stem rot resistance in soybean. Crop Sci. 29:672-674.
Poehlman, J.M. and Sleper, D.A., Methods in Plant Breeding, In Breeding Field Crops, $4^{th}$ ed. (1995), Iowa State University Press, pp. 172-174.
Narvel, et al., 2001. A Retrospective DNA Marker Assessment of the Development of Insect Resistant Soybean. Crop Sci. 41:1931-1939.
Goldman, et al., 1994. Molecular Markers Associated with Maize Kernel Oil Concentration in an Illinois High Protein x Illinois Low Protein Cross. Crop Sci. 34: 908-915.
Dierking, E. C., et al., "Raffinose and stachyose metabolism are not required for efficient soybean seed germination," Journal of Plant Physiology (2009).
Schlueter, J. A., et al., "Gene duplication and paleopolyploidy in soybean and the implications for whole genome sequencing," BMC Genomics (2007).
Dierking, E.C. and Bilyeu, K.D., "Association of a Soybean Raffinose Synthase Gene With Low Raffinose and Stachyose Seed Phenotype," The Plant Genome, 1(2): 135-145 (Nov. 21, 2008).
Dierking, E.C. and Bilyeu, K.D., "Glycine Max Raffinose Synthase 3 (RS3) Gene, Complete CDS," Database EMBL, XP002595342 (May 12, 2008).
Neus, J.D., et al., "Agronomic and Seed Characteristics of Soybean With Reduced Raffinose and Stachyose," Crop Science, 45(2): 589-592 (Feb. 23, 2005).
European Examiners Report; EP10 250 790.2-2403; Oct. 24, 2011; pp. 1-5.

* cited by examiner

SOYBEANS HAVING HIGH GERMINATION RATES AND ULTRA-LOW RAFFINOSE AND STACHYOSE CONTENT

REFERENCE TO RELATED APPLICATIONS

This application claims benefit under 35 U.S.C. §119 to U.S. application Ser. No. 61/170,048, filed Apr. 16, 2009, which is incorporated herein in its entirety by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 1463-012patentinsequence.

BACKGROUND OF THE INVENTION

The present invention relates to a mutant allele of soybean designated SG-ULRFO which results in an ultra-low raffinose and stachyose phenotype. The present invention also relates to a soybean seed, a soybean plant and parts of a soybean plant and a soybean hybrid which comprises the mutant allele. In addition, the present invention is directed to transferring the SG-ULRFO mutant allele to other soybean plants. The present invention also relates to novel polymorphisms of soybean raffinose synthase genes that associate with an ultra-low raffinose and stachyose phenotype. The present invention also relates to new soybeans having both an ultra-low raffinose and stachyose phenotype while having high germination rates. All publications cited in this application are herein incorporated by reference.

Soybean [*Glycine max* (L.) Merr.] represents one of the most important economic crops in the United States and is considered to be similar in importance to corn (*zea mays* L.) in acreage and second only to corn in value. Sleper and Poehlman (2006). The oil, protein, and carbohydrate composition of the soybean seed generally controls its use. Seeds of soybean cultivars in the United States have an average composition of 20% oil, 40% protein, and 15% soluble carbohydrates in dry weights of cotyledons of ungerminated seeds. Hsu, et al. (1973).

Soybean meal is a major component of the diets of monogastric animals and its usefulness is determined, in part, by the carbohydrate component. The carbohydrate component of soybean meal is comprised of three major oligosaccharides: sucrose, raffinose, and stachyose. Openshaw and Hadley (1978). Of the three, only sucrose is nutritionally useful and can be fully digested by monogastric animals. Raffinose and stachyose are considered anti-nutritional units because they cannot be digested due to the lack of α-galactosidase activity in the gut of monogastric animals. Removing raffinose and stachyose from soybean meal has been reported to increase the metabolizable energy of the diet by as much as 20%. Coon, et al. (1990). The effects of raffinose and stachyose in diets have been studied in pigs (Smiricky, et al. (2002)), dogs (Zuo, et al. (1996)), chickens (Parsons, et al. (2000)), and humans (Suarez, et al. (1999)). Generally, raffinose and stachyose are poorly digested by monogastrics; the removal of raffinose and stachyose from soybean meal increases the metabolizable energy of the diet and reduces flatulent production. Coon, et al. (1990); Parsons, et al. (2000); Suarez, et al. (1999).

Extensive botanical surveys of the occurrence of raffinose and stachyose have been reported in the scientific literature. See, Dey, P. M., In Biochemistry of Storage Carbohydrates in Green Plants, Academic Press, London, pp. 53-129 (1985). Raffinose and stachyose are thought to be second only to sucrose among the nonstructural carbohydrates with respect to abundance in the plant kingdom. In fact, raffinose and stachyose may be ubiquitous, at least among higher plants. Raffinose and stachyose accumulate in significant quantities in the edible portion of many economically significant crop species. Examples include soybean (*Glycine max* L. Merrill), sugar beet (*Beta vulgaris*), cotton (*Gossypium hirsutum* L.), canola (*Brassica* sp.), and all of the major edible leguminous crops, including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*), and lupine (*Lupinus* sp.).

The biosynthesis of raffinose and stachyose has been fairly well characterized. See, Dey, P. M., In Biochemistry of Storage Carbohydrates in Green Plants (1985). The committed reaction of raffinose and stachyose biosynthesis involves the synthesis of galactinol from UDP galactose and myo-inositol. The enzyme that catalyzes this reaction is galactinol synthase. Synthesis of raffinose and higher homologs in the raffinose and stachyose from sucrose is thought to be catalyzed by distinct galactosyltransferases (e.g., raffinose synthase, stachyose synthase, etc.).

In addition to evaluating plants at the molecular level, plant breeding is an important area in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. These important traits may include higher seed yield, resistance to diseases and insects, better stems and roots, tolerance to drought and heat, and better agronomic quality.

The complexity of inheritance influences choice of the breeding method when developing new soybean lines. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful lines produced per unit of input (e.g., per year, per dollar expended, etc.).

A most difficult task is the identification of lines that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

In addition to phenotypic observations, the genotype of a plant can also be examined. There are many laboratory-based techniques available for the analysis, comparison, and characterization of plant genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Soybean, *Glycine max* (L), is an important and valuable field crop. Thus, a continuing goal of soybean plant breeders is to develop stable, high yielding soybean lines with important commercial and agronomic traits.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

In one aspect, the invention provides for soybean seeds and plants having an ultra-low raffinose and stachyose content. Also provided are the parts of this plant, including, but not limited to, pollen, an ovule, and a cell. Further provided is a tissue culture of regenerable cells of the plant, wherein the tissue culture regenerates soybean plants capable of expressing all the physiological and morphological characteristics of the seed and plants of the present invention. In one embodiment of the invention, the regenerable cells are embryos, meristematic cells, pollen, leaves, roots, root tips or flowers or are protoplasts or callus derived therefrom. Further provided by the invention is a soybean plant or seed regenerated from the tissue culture capable of expressing all the physiological and morphological characteristics of the starting plant or seed.

In another aspect, the present invention provides a mutant allele designated SG-ULRFO derived from soybean that is phenotypically expressed by a low raffinose and stachyose seed content and high germination rates. The invention further provides for plants, seeds, and other plant parts, such as pollen and ovules, containing the mutant allele SG-ULRFO.

The invention also provides methods for introducing the allele of the present invention into plants by crossing a plant which lacks the mutant allele with a plant that has the allele, selfing the resulting generations and then selecting the plants exhibiting reduced levels of raffinose and stachyose seed content.

In another aspect, the present invention provides for an ultra-low raffinose seed content is defined as a raffinose seed content of from about 0% to about 0.13% by dry or wet weight of the total seed content, including from about 0.01%, 0.03%, 1.06%, 0.07%, 0.10%, 0.11% and 0.13%, including all integers and fractions thereof.

In another aspect of the invention, an ultra-low stachyose seed content is defined as a stachyose seed content of from about 0.19% to about 1.6% by dry or wet weight of the total seed content, including from about 0.1%, 0.2%, 0.4%, 0.55%, 0.73%, 0.85%, 0.91%, 1.05%, 1.06%, 1.08%, 1.1%, 1.15%, 1.19%, 1.23%, 1.33%, 1.37%, 1.42%, 1.46%, 1.49%, 1.52%, 1.56%, 1.59%, 1.6%, including all integers and fractions thereof.

In another aspect, the present invention provides for an ultra-low combined raffinose and stachyose seed content of from about 0.19% to about 1.75% by dry or wet weight of the total seed content, including from about 0.02%, 0.05%, 0.07%, 0.12%, 0.16%, 0.21%, 0.26%, 0.34%, 0.38%, 0.48%, 0.49%, 0.51%, 0.55%, 0.59%, 0.63%, 0.67%, 0.78%, 0.80%, 0.85%, 0.91%, 0.96%, 1.12%, 1.19%, 1.23%, 1.28%, 1.33%, 1.38%, 1.45%, 1.49%, 1.56%, 1.57%, 1.63%, 1.68%, 1.71%, 1.73%, 1.75%, including all integers and fractions thereof.

In another aspect, the present invention provide for an increased germination rate with the ultra-low raffinose and stachyose seed content, where the germination rates of said seeds is from about 83%, 84%, 85%, 86%, 87%, 88%, 89%, 90%, 91%, 92%, 93%, 94%, 95%, 96%, 97%, 98% and 99%, including all integers and fractions thereof.

In another aspect, the invention relates to a soybean plant or seed with a heritable phenotype of: (i) an ultra-low raffinose and stachyose seed content of less than 0.13% by dry or wet weight of the total seed content; (ii) an ultra-low stachyose seed content of less than 1.6% by dry or wet weight of the total seed content; and (iii) a seed germination rate of at least 83%.

Another aspect of the invention also provides methods for introducing the ultra-low raffinose and stachyose seed content of the present invention into other plants by crossing a plant which lacks the ultra-low raffinose and stachyose content phenotype with a plant that exhibits the ultra-low raffinose and stachyose seed content and then selecting the plants exhibiting the ultra-low raffinose and stachyose seed content.

In another aspect, the present invention provides for an isolated nucleic acid sequence that contributes to the ultra-low raffinose and stachyose seed content, as is shown in the nucleic acid sequence SEQ ID NO:3. A further aspect concerns an isolated polypeptide comprising an amino acid sequence, wherein the amino acid sequence comprises the amino acid sequence of SEQ ID NO:4.

In another aspect, the present invention provides for an isolated nucleic acid sequence that contributes to the ultra-low raffinose and stachyose seed content, as is shown in the DNA sequence SEQ ID NO:5. A further aspect concerns an isolated polypeptide comprising an amino acid sequence, wherein the amino acid sequence comprises the amino acid sequence of SEQ ID NO:6.

In another aspect, the present invention provides for a soybean seed having an ultra-low raffinose and stachyose seed content and containing the mutant nucleic acid sequence of RS2 (SEQ ID NO:1), the mutant nucleic acid sequence of RS3 (SEQ ID NO:3) and the mutant nucleic acid sequence of RS4 (SEQ ID NO:5).

In another aspect, the present invention relates to a chimeric gene comprising any of the isolated nucleic acid sequences of the present invention operably linked to a regulatory sequence, and a cell, a plant and a seed comprising the chimeric gene.

In another aspect, the present invention relates to a vector comprising any of the isolated nucleic acid sequences of the present invention.

In another aspect, the present invention provides for a method of producing soybean seeds with an ultra-low raffinose and stachyose seed content and having high germination rates. The method can involve crossing the ultra-low raffinose and stachyose and high germination rate soybean plants with another soybean not comprising these traits, harvesting the seed from said cross and selecting seed that have these desired traits for one or more generations. Where desired, the method may include assaying the progeny soybeans for the ultra-low raffinose and stachyose seed content and testing for high germination rates.

A further aspect of the present invention includes any such methods using soybean plants having an ultra-low raffinose and stachyose seed content and high germination rates as are a part of this invention: selfing, backcrosses, hybrid production, crosses to populations, and the like, and all plants produced using said soybean plants and seeds as at least one parent are within the scope of this invention.

In addition to the exemplary aspects and embodiments described above, further aspects and embodiments will become apparent by study of the following descriptions.

DEFINITIONS

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cell. Cell as used herein includes a plant cell, whether isolated, in tissue culture or incorporated in a plant or plant part.

Coding Sequence. Refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

Cotyledon. A cotyledon is a type of seed leaf. The cotyledon contains the food storage tissues of the seed.

Derived From. The term "derived from" includes genes, nucleic acids, and proteins when they include fragments or elements assembled in such a way that they produce a functional unit. The fragments or elements can be assembled from multiple organisms provided that they retain evolutionarily conserved function. Elements or domains could be assembled from various organisms and/or synthesized partially or entirely, provided that they retain evolutionarily conserved function, elements or domains. In some cases the derivation could include changes so that the codons are optimized for expression in a particular organism.

Embryo. The embryo is the small plant contained within a mature seed.

Expression. The term "expression", as used herein, refers to the transcription and stable accumulation of sense (mRNA) or antisense RNA derived from the nucleic acid fragment of the invention. Expression may also refer to translation of mRNA into a polypeptide.

Gene. As used herein, "gene" refers to a segment of nucleic acid. A gene can be introduced into a genome of a species, whether from a different species or from the same species, using transformation or various breeding methods.

Gene Silencing. The interruption or suppression of the expression of a gene at the level of transcription or translation.

Genotype. Refers to the genetic constitution of a cell or organism.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the plant by backcrossing, a natural or induced mutation, or a transgene introduced through genetic transformation techniques. A locus may comprise one or more alleles integrated at a single chromosomal location.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Oligosaccharide. An oligosaccharide means a saccharide containing three to ten components (rings).

Phenotype. The detectable characteristics of a cell or organism, which characteristics are the manifestation of gene expression.

Plant. As used herein, the term "plant" includes reference to an immature or mature whole plant, including a plant from which seed or grain or anthers have been removed. Seed or embryo that will produce the plant is also considered to be the plant.

Plant Parts. As used herein, the term "plant parts" (or a soybean plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an $F_1$ soybean plant produced from the cross of two soybean plants where at least one plant includes a soybean plant of the present invention and progeny further includes but is not limited to subsequent $F_2$, $F_3$, $F_4$, $F_5$, $F_6$, $F_7$, $F_8$, $F_9$, and $F_{10}$ generational crosses with the recurrent parental line.

Protein or Polypeptide. A "protein" or "polypeptide" is a chain of amino acids arranged in a specific order determined by the coding sequence in a polynucleotide encoding the polypeptide. Each protein or polypeptide has a unique function.

Quantitative Trait Loci (QTL). Quantitative trait loci (QTL) refer to genetic loci that control to some degree numerically representable traits that are usually continuously distributed.

Raffinose. Raffinose is a trisaccharide, 3-ringed molecule, composed of glucose, fructose, and galactose.

Recombinant polynucleotide. The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Regeneration. Regeneration refers to the development of a plant from tissue culture.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stachyose. Stachyose is a tetrasaccharide, 4-ringed molecule, composed of glucose, fructose, and two galactose molecules.

Sucrose. Sucrose is a disaccharide composed of fructose and glucose (table sugar).

BRIEF DESCRIPTION OF THE FIGURES

Exemplary embodiments are illustrated in referenced Figures. It is intended that the embodiments and Figures disclosed herein are to be considered illustrative rather than limiting.

BRIEF DESCRIPTION OF THE SEQUENCE LISITINGS

Figure 1:
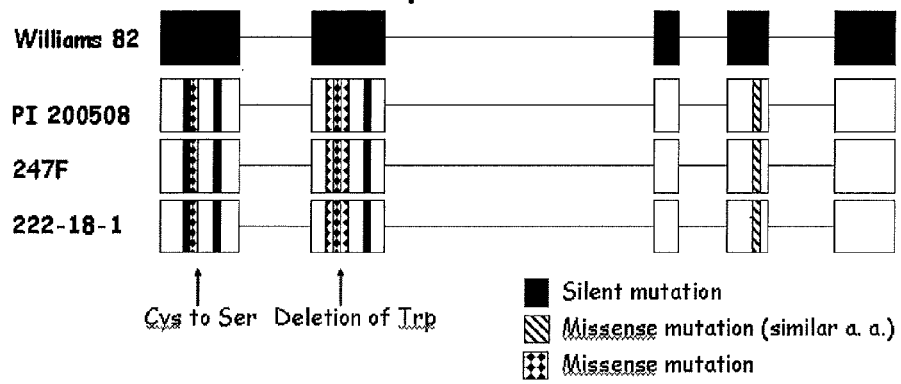
FIG. 1 compares the mutant RS2 amino acid sequence with a wild-type (control) line, Williams 82, a public line, PI 200508 and soybean lines 247F and 222-18-1, wherein line 222-18-1 of the present invention has the ultra-low raffinose and stachyose seed content and high germination rates.
Figure 2:
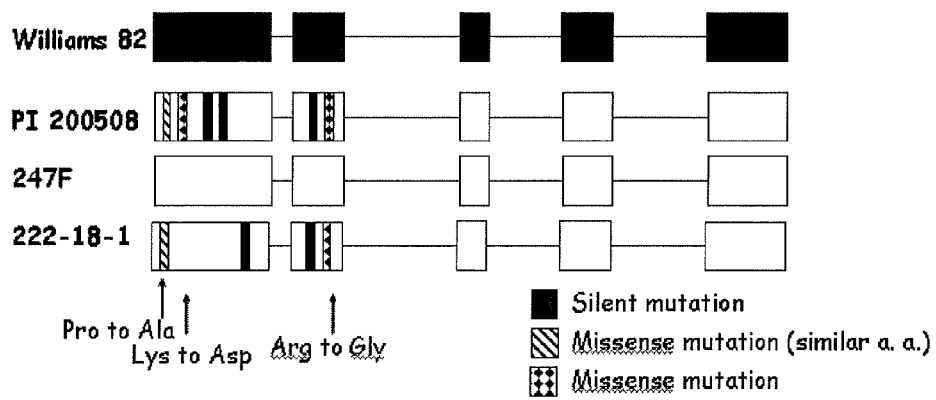
FIG. 2 compares the mutant RS3 amino acid sequence with a wild-type (control) line, Williams 82, a public line, PI 200508 and the soybean lines 247F and 222-18-1, wherein line 222-18-1 of the present invention has the ultra-low raffinose and stachyose seed content and high germination rates.
Figure 3:
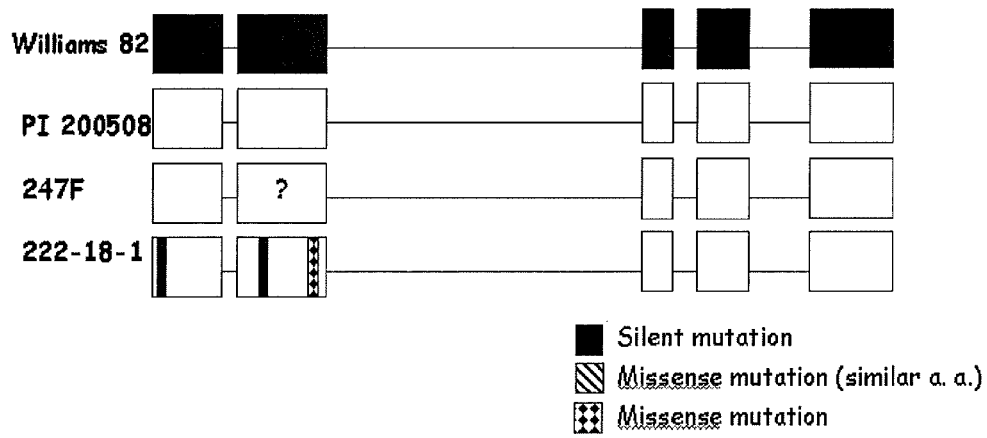
FIG. 3 compares the mutant RS4 amino acid sequence with a wild-type (control) line, Williams 82, a public line, PI 200508 and the soybean lines 247F and 222-18-1, wherein line 222-18-1 of the present invention has the ultra-low raffinose and stachyose seed content and high germination rates.

SEQ ID NO:1 shows the nucleic acid sequence to the mutant raffinose synthase gene RS2.

SEQ ID NO:2 shows the amino acid sequence to the mutant raffinose synthase gene RS2.

SEQ ID NO:3 shows the nucleic acid sequence to the mutant raffinose synthase gene RS3.

SEQ ID NO:4 shows the amino acid sequence to the mutant raffinose synthase gene RS3.

SEQ ID NO:5 shows the nucleic acid sequence to the mutant raffinose synthase gene RS4.

SEQ ID NO:6 shows the amino acid sequence to the mutant raffinose synthase gene RS4.

SEQ ID NO:7 shows the nucleic acid sequence to a primer for genotyping (SNP marker assay) raffinose synthase gene RS2.

SEQ ID NO:8 shows the nucleic acid sequence to a primer for genotyping (SNP marker assay) raffinose synthase gene RS2.

SEQ ID NO:9 shows the nucleic acid sequence to a primer for genotyping (SNP marker assay) raffinose synthase gene RS2.

SEQ ID NO:10 shows the nucleic acid sequence to an expression primer for raffinose synthase gene RS2.

SEQ ID NO:11 shows the nucleic acid sequence to an expression primer for raffinose synthase gene RS2.

SEQ ID NO:12 shows the nucleic acid sequence to a primer for genotyping (SNP marker assay) raffinose synthase gene RS3.

SEQ ID NO:13 shows the nucleic acid sequence to a primer for genotyping (SNP marker assay) raffinose synthase gene RS3.

SEQ ID NO:14 shows the nucleic acid sequence to a primer for genotyping (SNP marker assay) raffinose synthase gene RS3.

SEQ ID NO:15 shows the nucleic acid sequence to an expression primer for raffinose synthase gene RS3.

SEQ ID NO:16 shows the nucleic acid sequence to an expression primer for raffinose synthase gene RS3.

SEQ ID NO:17 shows the nucleic acid sequence to an expression primer for a housekeeping elongation factor 1α (used for expression analysis and as a control).

SEQ ID NO:18 shows the nucleic acid sequence to an expression primer for a housekeeping elongation factor 1α (used for expression analysis and as a control).

DETAILED DESCRIPTION OF THE INVENTION

Although abundant in many species, raffinose family oligosaccharides, i.e., raffinose, stachyose, and verbascose (and also known as RFOs), are an obstacle to the efficient utilization of some economically important crop species. Raffinose and stachyose are not digested directly by animals, primarily because a-galactosidase is not present in the intestinal mucosa. Gitzelmann and Auricchio, *Pediatrics,* 36:231-236 (1965); Rutloff, et al., Nahrung, 11:39-46 (1967). However, microflora in the lower gut are readily able to ferment the raffinose and stachyose which results in an acidification of the gut and production of carbon dioxide, methane and hydrogen. Murphy, et al., J. *Agr. Food Chem.,* 20:813-817 (1972); Cristofaro, et al., In Sugars in Nutrition, Chapter 20, 313-335 (1974); Reddy, et al., *J. Food Science,* 45:1161-1164 (1980). The presence of raffinose and stachyose restricts the use of soybeans in animal, including human, diets because otherwise this species is an excellent source of protein and fiber. Additionally, RFOs are thought to be an important source of energy during seed germination. In contrast to their potential for promoting germination, RFOs represent anti-nutritional units for monogastric animals when consumed as a component of feed.

Although the exact function of RFOs in germinating seeds is largely unknown, it is clear that seeds require a large amount of energy during germination. Bewley and Black (1994). This energy is hypothesized to come from stored carbohydrates. Sucrose and RFOs are the most abundant of the soluble sugars (Peterbauer and Richter (2001)), but account for only a small portion of the total carbohydrates present in the seeds (Ziegler, 1995). The problems and costs associated with RFOs could be reduced or eliminated through the availability of genes that confer a reduction of RFO content of soybean seeds. Such genes could be used to develop soybean varieties having inherently reduced and ultra-low levels of raffinose and stachyose seed content. Soybean varieties with inherently reduced RFO content would improve the nutritional quality of derived soy protein products and reduce processing costs associated with the removal of RFOs. Soybean varieties with an ultra-low RFO content would be more valuable than conventional varieties for animal and human diets and would allow mankind to more fully utilize the desirable nutritional qualities of this edible legume. Thus, developing a soybean product with commercially significance properties is a high priority in most soybean cultivar development programs.

The key step in raffinose and stachyose biosynthesis is mediated by the enzyme raffinose synthase. The raffinose synthase enzyme belongs to a group of hydrolase family enzymes that execute a galactosyl transfer from galactinol to sucrose. This transfer produces the three ring molecule raffinose; myo-inositol is formed as a by-product. Similarly, stachyose is formed by the action of stachyose synthase which combines raffinose and galactinol. Thus, raffinose synthase and stachyose synthase share one identical substrate, galactinol, and a second similar substrate, sucrose or raffinose, respectively. It is not known if raffinose synthase and stachyose synthase have overlapping enzymatic activity in soybean.

The exact role for RFOs during soybean seed development and germination has not been determined but it has been theorized that RFOs are required for successful germination. See Obendorf, R. L., et al., *Crop Science.*, 48:2396-2403 (2008); Obendorf, R. L., et al., *Crop Science.*, 49:329-341 (2009); and U.S. Pat. No. 6,147,193.

The prior art has failed to provide plants of such characteristics, presumably because of the difficulty in combining the ultra-low RFO phenotype with commercially acceptable germination rates. By describing methods for the production of such plants and providing examples of these plants, the invention now allows the preparation of a potentially unlimited number of novel soybean varieties exhibiting commercially significant ultra-low raffinose and stachyose seed content. Once such a soybean variety is produced, the desired phenotype can be transferred to other soybean varieties with appropriate backcross and selection to maintain the desirable traits as described herein.

The present invention relates to a new mutant allele designated SG-ULRFO in the genus *Glycine* that is phenotypically expressed as an ultra-low raffinose and stachyose seed content and having high germination rates. The present invention also relates to a soybean seed, a soybean plant and plant parts which comprise the mutant allele SG-ULRFO. The present invention also relates to a method of producing the soybean plants and seeds.

The SG-ULRFO mutant allele of the present invention can be introgressed into any plant or seed lacking the mutant allele. The mutant allele and the methods of the present invention can be used to modify the raffinose and stachyose seed content of soybean seeds for commercial production. Generally, the methods involve controlled bud pollination or ovule culture. The crosses can be performed using either parent as the pollen parent.

A plant of the present invention can be obtained by crossing a plant having the SG-ULRFO mutant allele with any plant lacking the mutant allele.

Other breeding schemes can be used to introduce the SG-ULRFO mutant allele into the desired soybean plant. The particular scheme used is not critical to the invention, so long as the allele is stably incorporated into the genome of the soybean plant or seed. For example, a marker gene can be used. A nucleic acid probe which hybridizes to the marker gene can be used to identify the desired plants in the $F_1$ generation.

The SG-ULRFO mutant allele will advantageously be introduced into varieties that contain other desirable genetic traits such as resistance to disease or pests, drought tolerance, and the like.

The present invention also relates to methods for producing a soybean plant or a containing in its genetic material one or more transgenes and to the transgenic soybean plant produced by that method. Preferably the transgene is the SG-ULRFO mutant allele or cDNA of the SG-ULRFO mutant allele.

The present invention describes soybean seeds and plants having an ultra-low raffinose and stachyose seed content. Also provided are the parts of this plant, including, but not limited to, pollen, an ovule, and a cell. Further provided is a tissue culture of regenerable cells of the plant, wherein the tissue culture regenerates soybean plants capable of expressing all the physiological and morphological characteristics of the seed and plants of the present invention. In one embodiment of the invention, the regenerable cells are embryos, meristematic cells, pollen, leaves, roots, root tips or flowers or are protoplasts or callus derived therefrom. Further provided by the invention is a soybean plant or seed regenerated from the tissue culture capable of expressing all the physiological and morphological characteristics of the starting plant or seed.

In accordance with the present invention, an ultra-low raffinose seed content is defined as a raffinose seed content of from about 0% to about 0.13% by dry or wet weight of the total seed content, including from about 0.01%, 0.03%, 1.06%, 0.07%, 0.10%, 0.11% and 0.13%, including all integers and fractions thereof.

In another embodiment of the present invention, an ultra-low stachyose seed content is defined as a stachyose seed content of from about 0.19% to about 1.6% by dry or wet weight of the total seed content, including from about 0.1%, 0.2%, 0.4%, 0.55%, 0.73%, 0.85%, 0.91%, 1.05%, 1.06%, 1.08%, 1.1%, 1.15%, 1.19%, 1.23%, 1.33%, 1.37%, 1.42%, 1.46%, 1.49%, 1.52%, 1.56%, 1.59%, 1.6%, including all integers and fractions thereof.

In another embodiment, the present invention provides for an ultra-low combined raffinose and stachyose seed content of from about 0.19% to about 1.75% by dry or wet weight of the total seed content, including from about 0.02%, 0.05%, 0.07%, 0.12%, 0.16%, 0.21%, 0.26%, 0.34%, 0.38%, 0.48%, 0.49%, 0.51%, 0.55%, 0.59%, 0.63%, 0.67%, 0.78%, 0.80%, 0.85%, 0.91%, 0.96%, 1.12%, 1.19%, 1.23%, 1.28%, 1.33%, 1.38%, 1.45%, 1.49%, 1.56%, 1.57%, 1.63%, 1.68%, 1.71%, 1.73%, 1.75%, including all integers and fractions thereof.

In another embodiment, the present invention provides for an increased germination rate for soybean seed with the ultra-low raffinose and stachyose seed content, where the germination rates of said seeds is from about 83%, 84%, 85%, 86%, 87%, 88%, 89%, 90%, 91%, 92%, 93%, 94%, 95%, 96%, 97%, 98% and 99%, including all integers and fractions thereof.

In another embodiment, the present invention provides for a nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99% or 100% identity to the nucleotide sequence of SEQ ID NO:1. A further aspect concerns a polypeptide comprising an amino acid sequence, wherein the amino acid sequence comprises an amino acid sequence 60%, preferably at least about 70%, more preferably at least about 80% and most preferably at least about 90%, 91%, 92%, 93%, 94%, 95%, 96%, 97%, 98%, 99%, or 100% identity to and having the same function as the amino acid sequence of SEQ ID NO:2.

In another embodiment, the present invention provides for an isolated nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99%, or 100% identity to the nucleotide sequence of SEQ ID NO:3. A further aspect concerns a polypeptide comprising an amino acid sequence, wherein the amino acid sequence comprises an amino acid sequence 60%, preferably at least about 70%, more preferably at least about 80% and most preferably at least about 90%, 91%, 92%, 93%, 94%, 95%, 96%, 97%, 98%, 99%, or 100% identity to and having the same function as the amino acid sequence of SEQ ID NO:4.

In another embodiment, the present invention provides for a nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99%, or 100% identity to the nucleotide sequence of SEQ ID NO:5. A further aspect concerns a polypeptide, wherein the amino acid sequence comprises an amino acid sequence 60%, preferably at least about 70%, more preferably at least about 80% and most preferably at least about 90%, 91%, 92%, 93%, 94%, 95%, 96%, 97%, 98%, 99%, or 100% identity to and having the same function as the amino acid sequence of SEQ ID NO:6.

In another embodiment, the present invention provides for the ultra-low raffinose and stachyose seed content containing a nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99%, or 100% identity to the nucleotide sequence of RS2 (SEQ ID NO:1) and a nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99%, or 100% identity to the nucleotide sequence of RS3 (SEQ ID NO:3) and a nucleic acid sequence that contributes to the ultra-low raffinose and stachyose seed content, which has at least about 60%, preferably at least about 70%, more preferably at least about 80% and most preferably at least about 90%, 91%, 92%, 93%, 94%, 95%, 96%, 97%, 98%, 99%, or 100% identity to the nucleotide sequence of RS4 (SEQ ID NO:5).

In another embodiment, the present invention provides a soybean seed comprising an amino acid sequence encoding an RS2 polypeptide having the amino acid sequence as set forth in SEQ ID NO:2 and an amino acid sequence encoding an RS4 polypeptide having the amino acid sequence as set forth in SEQ ID NO. 6. Further, the present invention provides for a soybean seed comprising an amino acid sequence encoding an RS2 polypeptide having the amino acid sequence as set forth in SEQ ID NO:2 and an amino acid sequence encoding an RS3 polypeptide having the amino acid sequence as set forth in SEQ ID NO. 4. The present invention also provides for a soybean seed comprising an amino acid sequence encoding an RS2 polypeptide having the amino acid sequence as set forth in SEQ ID NO:2, an amino acid sequence encoding an RS3 polypeptide having the amino acid sequence as set forth in SEQ ID NO. 4 and an amino acid sequence encoding an RS4 polypeptide having the amino acid sequence as set forth in SEQ ID NO. 6.

Polymerase Chain Reaction (PCR) is a repetitive, enzymatic, primed synthesis of a nucleic acid sequence. This procedure is well-known and commonly used by those skilled in the art. See, Mullis, U.S. Pat. Nos. 4,683,195, 4,683,202, and 4,800,159; Saiki, et al., Science, 230:1350-1354 (1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium, *Thermus aquaticus*, the amplification process can be completely automated. Other enzymes which can be used are known to those skilled in the art.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook, et al., Molecular Cloning, Second Edition, Cold Spring Harbor Laboratory, Plainview, N.Y. (1989); Maniatis, et al., Molecular Cloning, Cold Spring Harbor Laboratory, Plainview, N.Y. (1982); Wu (ed.), *Meth. Enzymol.*, 218, Part I (1993); Wu (ed.), *Meth. Enzymol.*, 68 (1979); Wu, et al. (eds.), *Meth. Enzymol.*, 100 and 101 (1983); Grossman and Moldave (eds.), *Meth. Enzymol.*, 65; Miller (ed.), Experiments in Molecular Genetics, Cold Spring Harbor Laboratory, Cold Spring Harbor, N.Y. (1972); Old and Primrose, Principles of Gene Manipulation, University of California Press, Berkley (1981); Schleif and Wensink, Practical Methods in Molecular Biology (1982); Glover (ed.), DNA Cloning, Vols. I and II, IRL Press, Oxford, UK (1985); Hames and Higgins (eds.), Nucleic Acid Hybridization, IRL Press, Oxford, UK (1985); Setlow and Hollaender, Genetic Engineering: Principles and Methods, Vols. 1-4, Plenum Press, New York (1979); and Ausubel, et al., Current Protocols in Molecular Biology, Greene/Wiley, N.Y. (1992). Abbreviations and nomenclature, where employed, are deemed standard in the field and commonly used in professional journals such as those cited herein. Intermediate cloning of the PCR products can be done using the PCRTerminator end repair kit and CLoneSmart kit vector pSMART (Lucigen, Middleton, Wis.). Various PCR based cloning methods are known to those skilled in the art.

It is well-known in the art that the nucleic acid sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well-known. In addition, it is well-known that Bal31 exonuclease can be conveniently used for time-controlled limited digestion of DNA. See, for example, Maniatis, *Molecular Cloning: A Laboratory Manual*, Cold Spring Harbor Laboratory, New York, pp. 135-139 (1982), incorporated herein by reference. See also, Wei, et al., *J. Biol. Chem.*, 258:13006-13512 (1983). By use of Bal31 exonuclease (commonly referred to as Aerase-a-base procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along a starting nucleotide sequence. The ordinarily skilled artisan can routinely test or screen the generated fragments for their characteristics and determine the utility of the fragments as taught herein. It is also well-known that the mutant sequences of the full length sequence, or fragments thereof, can be easily produced with site directed mutagenesis. See, for example, Larionov, O. A. and Nikiforov, V. G., *Genetika*, 18(3):349-59 (1982); Shortie, D., DiMaio, D., and Nathans, D., *Annu. Rev. Genet.*, 15:265-94 (1981); both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain promoter activity. It is well-known in the art that there are a variety of other PCR-mediated methods, such as overlapping PCR that may be used.

A nucleic acid sequence or polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

Identity means the degree of sequence relatedness between two polypeptides or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans. Lesk, A. M., (ed.), Computational Molecular Biology, Oxford University Press, New York (1988); Smith, D. W., (ed.), Biocomputing: Informatics and Genome Projects, Academic Press, New York (1993); Griffin, A. M., and Griffin, H. G., (eds.), Computer Analysis of Sequence Data, Part I, Humana Press, New Jersey (1994); von Heinje, G., Sequence Analysis in Molecular Biology, Academic Press (1987); and Gribskov, M. and Devereux, J., (eds.), Sequence Analysis Primer, M Stockton Press, New York (1991). Methods commonly employed to determine identity between two sequences include, but are not limited to, those disclosed in Guide to Huge Computers, Martin J. Bishop, (ed.), Academic Press, San Diego (1994), and Carillo, H., and Lipman, D., SIAM J Applied Math., 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison, Wis.), program package (Devereux, J., et al., Nucleic Acids Research, 12:387 (1984)), BLASTP, BLASTN, FASTA (Altschul, et al., (1990); Altschul, et al., (1997)). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

In another embodiment, the present invention provides for host cells or viruses comprising a chimeric gene of one or more of the isolated nucleic acid sequences of the present invention operably linked to a regulatory sequence, and a cell, a plant and a seed comprising the chimeric gene. Examples of host cells which can be used to practice the invention include, but are not limited to, yeast, bacteria, and plants.

A nucleotide sequence is operably linked when it is placed into a functional relationship with another nucleotide sequence. For instance, a promoter is operably linked to a coding sequence if the promoter effects the transcription or expression of the coding sequence. Operably linked also means that the sequences being linked are contiguous and, where necessary to join two protein coding regions, contiguous and in reading frame; and for example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. However, it is well-known that certain genetic elements, such as enhancers, may be operably linked even at a distance, i.e., even if not contiguous.

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include, but are not limited to, those from the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

Suitable constitutive promoters for use in plants include promoters from plant viruses, such as the peanut chlorotic streak caulimovirus (PC1SV) promoter (U.S. Pat. No. 5,850, 019), the 35S promoter from cauliflower mosaic virus (CaMV) (Odell, et al., *Nature*, 313:810-812 (1985)), promoters of Chlorella virus methyltransferase genes (U.S. Pat. No. 5,563,328), and the full-length transcript promoter from figwort mosaic virus (FMV) (U.S. Pat. No. 5,378,619); the promoters from such genes as rice actin (McElroy, et al., *Plant Cell*, 2:163-171 (1990)), ubiquitin (Christensen, et al., *Plant Mol. Biol.*, 12:619-632 (1989) and Christensen, et al., *Plant Mol. Biol.*, 18:675-689 (1992)), pEMU (Last, et al., *Theor. Appl. Genet.*, 81:581-588 (1991)), MAS (Velten, et al., *EMBO J.*, 3:2723-2730 (1984)), maize H3 histone (Lepetit, et al., *Mol. Gen. Genet.*, 231:276-285 (1992) and Atanassova, et al., *Plant Journal*, 2(3):291-300 (1992)), *Brassica napes* ALS3 (WO 97/41228); and promoters of various *Agrobacterium* genes (see, U.S. Pat. Nos. 4,771,002, 5,102,796, 5,182, 200, and 5,428,147). Finally, promoters composed of portions of other promoters and partially or totally synthetic promoters can be used. See, e.g., Ni, et al., *Plant J.*, 7:661-676 (1995) and WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316), and the FMV enhancer element (Maiti, et al., *Transgenic Res.*, 6:143-156 (1997)). See also, WO 96/23898 and *Enhancers and Eukaryotic Expression*, Cold Spring Harbor Press, Cold Spring Harbor, N.Y. (1983).

In another embodiment, the present invention provides for using the nucleic acid sequences of the present invention to create transgenic plants and seeds in which certain oligosaccharides are present at lower levels than in normal or wild type plants and seeds. This would, for example, have the effect of lowering the raffinose and stachyose seed level in soybean seeds and increasing the sucrose level.

The regeneration, development, and cultivation of plants from single plant protoplast transformants or from various transformed explants is also well-known in the art. Weissbach and Weissbach, (eds.), In: Methods for Plant Molecular Biology, Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing an ultra-low raffinose and stachyose content is cultivated using methods well-known to one skilled in the art.

There are a variety of methods for the regeneration of plants from plant tissue. The particular method of regeneration will depend on the starting plant tissue and the particular plant species to be regenerated.

Methods for transformation to obtain transgenic plants are well-known and have been published for soybean (U.S. Pat. Nos. 6,576,820, 5,569,834, 5,416,011; McCabe, et. al., *BiolTechnology*, 6:923 (1988); Christou, et al., *Plant Physiol.*, 87:671-674 (1988)); cotton (U.S. Pat. Nos. 5,004,863, 5,159, 135, 5,518,908); *Brassica* (U.S. Pat. No. 5,463,174); peanut (Cheng, et al., *Plant Cell Rep.*, 15:653-657 (1996); McKently, et al., *Plant Cell Rep.*, 14:699-703 (1995)); papaya and pea (Grant, et al., *Plant Cell Rep.*, 15:254-258 (1995)).

A DNA construct can be used to transform any type of plant or plant cell. A genetic marker can be used for selecting transformed plant cells ("a selection marker"). Selection markers typically allow transformed cells to be recovered by negative selection (ie, inhibiting growth of cells that do not contain the selection marker) or by screening for a product encoded by the selection marker. The most commonly used selectable marker gene for plant transformation is the neomycin phosphotransferase II (nptII) gene, isolated from Tn5, which, when placed under the control of plant expression control signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985). Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides, such as glyphosate, glufosinate, or bromoxynil. Comai, et al., *Nature*, 317:741-744 (1985); Stalker, et al., *Science*, 242:419-423 (1988); Hinchee, et al., *Bio/Technology*, 6:915-922 (1988); Stalker, et al., *J. Biol. Chem.*, 263:6310-6314 (1988); and Gordon-Kamm, et al., *Plant Cell*, 2:603-618 (1990).

Additional selectable markers useful for plant transformation include, without limitation, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., Science, 233:478 (1986); Charest, et al., *Plant Cell Rep.*, 8:643 (1990); EP 154,204.

Commonly used genes for screening presumptively transformed cells include, but are not limited to, β-glucuronidase (GUS), β-galactosidase, luciferase, and chloramphenicol acetyltransferase (Jefferson, R. A., *Plant Mol. Biol. Rep.*, 5:387 (1987); Teen, et al., *EMBO J.*, 8:343 (1989); Koncz, et al., *Proc. Natl. Acad. Sci. USA*, 84:131 (1987); De Block, et al., *EMBO J.*, 3:1681 (1984)), green fluorescent protein (GFP) and its variants (Chalfie, et al., *Science*, 263:802 (1994); Haseloff, et al., TIG, 11:328-329 (1995), and WO 97/41228). Another approach to the identification of relatively rare transformation events has been use of a gene that encodes a dominant constitutive regulator of the *Zea mays* anthocyanin pigmentation pathway (Ludwig, et al., Science, 247:449 (1990)).

Assays for gene expression based on the transient expression of cloned nucleic acid constructs have been developed by introducing the nucleic acid molecules into plant cells by polyethylene glycol treatment, electroporation, or particle bombardment (Marcotte, et al., Nature, 335:454-457 (1988); Marcotte, et al., *Plant Cell*, 1:523-532 (1989); McCarty, et al., Cell, 66:895-905 (1991); Hattori, et al., *Genes Dev.*, 6:609-618 (1992); Goff, et al., *EMBO J.*, 9:2517-2522 (1990)).

Transient expression systems may be used to functionally dissect isolated nucleic acid fragment constructs (see generally, Maliga, et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers, etc.

In addition to the above discussed procedures the standard resource materials which describe specific conditions and procedures for the construction, manipulation and isolation of macromolecules (e.g., DNA molecules, plasmids, etc.), generation of recombinant organisms and screening and isolating of clones (see, for example, Sambrook, et al., Molecular Cloning: A Laboratory Manual, Cold Spring Harbor Press (1989); Maliga, et al., Methods in Plant Molecular Biology, Cold Spring Harbor Press (1995); Birren, et al., Genome Analysis: Detecting Genes, 1, Cold Spring Harbor, N.Y. (1998); Birren, et al., Genome Analysis: Analyzing DNA, 2, Cold Spring Harbor, N.Y. (1998); Clark, Springer (eds.), Plant Molecular Biology: A Laboratory Manual, New York (1997)) are well known.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' non-coding sequences encoding transcription termination signals may also be provided. The instant recombinant DNA construct may also comprise one or more introns in order to facilitate gene expression of the recombinant DNA construct.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or co-suppression (U.S. Pat. Nos. 5,190,931, 5,107,065, and 5,283,323). An antisense or co-suppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene(s) is(are) ordinarily expressed.

The person skilled in the art will know that special considerations are associated with the use of antisense or co-suppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention relates to a vector comprising one or more of the isolated nucleic acid sequences of the present invention. A further embodiment of the present invention includes a vector containing a gene encoding one or more of the nucleic acid sequences of the present invention is introduced into soybeans.

Plasmid vectors comprising the instant isolated polynucleotides (or recombinant DNA constructs) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or recombinant DNA construct. The skilled artisan will also recognize that different independent transformation events will result in different levels and patterns of expression (Jones, et al., *EMBO J.*, 4:2411-2418 (1985); De Almeida, et al., *Mol. Gen. Genetics*, 218:78-86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

An appropriate promoter and other necessary vector sequences will be selected so as to be functional in the host. Examples of workable combinations of cell lines and expression vectors are described in Sambrook, et al., vide infra (1989); Ausubel, et al., (eds.), *Current Protocols in Molecular Biology*, Greene Publishing and Wiley Interscience, New York (1995); and Metzger, et al., Nature, 334: 31-36 (1988). Many useful vectors for expression in bacteria, yeast, fungal, mammalian, insect, plant, or other cells are well-known in the art and may be obtained from vendors such as Stratagene, New England Biolabs, Promega Biotech, CAMBIA and others. In addition, the construct may be joined to an amplifiable gene so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that: (a) confer resistance to antibiotics or other toxic substances, e.g., ampicillin, neomycin, methotrexate, kanamycin, hygromycin, BASTA, glyphosate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule. The DNA can be introduced by any means known to the art which is appropriate for the particular type of cell, or plant or eukaryotic organisms, including without limitation, *Agrobacterium*-mediated, bacterial mediated, transformation, lipofection, particle bombardment, or electroporation.

It is recognized by those skilled in the art that the DNA sequences may vary due to the degeneracy of the genetic code and codon usage.

In another aspect, the present invention provides for a method of producing soybean seeds with an ultra-low raffinose and stachyose seed content and having high germination rates. The method can involve traditional breeding techniques such as crossing the ultra-low raffinose and stachyose and high germination rate soybean plants with another soybean not comprising these traits, harvesting the seed from said cross and selecting seed that have these desired traits for one or more generations. Where desired, the method may include assaying the progeny soybeans for the ultra-low raffinose and stachyose seed content and testing for high germination rates.

Another aspect of the present invention includes any such breeding methods using soybean plants of the present invention that have an ultra-low raffinose and stachyose seed content and high germination rates are part of this invention: selfing, backcrosses, hybrid production, crosses to populations, and the like, and all plants produced using said soybean plants as at least one parent are within the scope of this invention.

The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper (1994); Fehr, Principles of Cultivar Development, pp. 261-286 (1987)). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Several of these single gene traits are described in U.S. Pat. Nos. 5,959,185, 5,973,234, and 5,977,445, the disclosures of which are specifically hereby incorporated by reference.

A backcross conversion of soybean plants of the present invention occurs when DNA sequences are introduced through backcrossing (Hallauer, et al., "Corn Breeding," *Corn and Corn Improvements*, No. 18, pp. 463-481 (1988)), with soybean cultivar 247F and 222-181-1 utilized as the recurrent parent. Both naturally occurring and transgenic DNA sequences may be introduced through backcrossing techniques. A backcross conversion may produce a plant with a trait or locus conversion in at least two or more backcrosses, including at least two crosses, at least three crosses, at least four crosses, at least five crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, In: *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See, Hallauer, et al., *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance, and herbicide resistance. In addition, an introgression site itself, such as an FRT site, Lox site or other site specific integration site, may be inserted by backcrossing and utilized for direct insertion of one or more genes of interest into a specific plant variety. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selling the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the desired phenotype. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

The new soybean plants of the present invention also provide a source of breeding material that may be used to develop other new soybean varieties. Plant breeding techniques known in the art and used in a soybean plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of soybean varieties in a plant breeding program requires, in general, the development and evaluation of homozygous varieties. There are many analytical methods available to evaluate a new variety. The oldest and most traditional method of analysis is the observation of phenotypic traits but genotypic analysis may also be used.

This invention also is directed to methods for producing a soybean plant by crossing a first parent soybean plant with a second parent soybean plant wherein either the first or second parent soybean plant contains the SG-ULRFO mutant allele of the present invention. Further, this invention also is directed to methods for producing a soybean SG-ULRFO mutant allele derived soybean plant by crossing a soybean line containing the SG-ULRFO mutant allele with a second soybean plant and growing the progeny seed, and repeating the crossing and growing steps with the soybean SG-ULRFO mutant allele derived plant from 1, 2, 3, 4, 5, 6 to 7 times. Thus, any such methods using a soybean line containing the SG-ULRFO mutant allele are part of this invention: selfing, backcrosses, hybrid production, crosses to populations, and the like. All plants produced using a soybean line containing the SG-ULRFO mutant allele as a parent are within the scope of this invention, including plants derived from soybean lines having the SG-ULRFO mutant allele. These methods are well-known in the art and some of the more commonly used breeding methods are described below. Descriptions of breeding methods can be found in one of several reference books (e.g., Allard, Principles of Plant Breeding (1960); Simmonds, Principles of Crop Improvement (1979); Sneep, et al., (1979); Fehr, "Breeding Methods for Cultivar Development," Chapter 7, Soybean Improvement, Production and Uses, 2nd ed., Wilcox editor (1987).

The following describes breeding methods that may be used with the soybean plants of the present invention in the development of further soybean plants. One such embodiment is comprised of: obtaining the soybean plant, or a part thereof, of the soybean plant of the present invention, utilizing said plant or plant part as a source of breeding material and selecting a soybean progeny plants with molecular markers in common with soybean plants of the present invention and/or with morphological and/or physiological. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example, SSR markers) and the making of double haploids may be utilized.

One of ordinary skill in the art of plant breeding would know how to evaluate the traits of soybean plants of the present invention to determine if there is no significant difference between the traits expressed by the soybean plants of the present invention and other soybean plants.

Pedigree breeding starts with the crossing of two genotypes if the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the nonrecurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new soybean varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Traditional breeding techniques can be enhanced through the use of molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing the soybean plants of the present invention.

Isozyme Electrophoresis and RFLPs have been widely used to determine genetic composition. Shoemaker and Olsen, Molecular Linkage Map of Soybean (*Glycine max* L. Men.), pp. 6.131-6.138 (1993). In S. J. O'Brien, (ed.), *Genetic Maps: Locus Maps of Complex Genomes*, Cold Spring Harbor Laboratory Press, Cold Spring Harbor, N.Y., developed a molecular genetic linkage map that consisted of twenty-five linkage groups with about 365 RFLP, 11 RAPD (random amplified polymorphic DNA), three classical markers, and four isozyme loci. See also, Shoemaker, R. C., RFLP Map of Soybean, pp. 299-309 (1994); In Phillips, R. L. and Vasil, I. K. (ed.), *DNA-based markers in plants*, Kluwer Academic Press Dordrecht, the Netherlands.

SSR technology is currently the most efficient and practical marker technology; more marker loci can be routinely used and more alleles per marker locus can be found using SSRs in comparison to RFLPs. For example, Diwan and Cregan described a highly polymorphic microsatellite loci in soybean with as many as 26 alleles. (Diwan, N. and Cregan, P. B., Automated sizing of fluorescent-labelled simple sequence repeat (SSR) markers to assay genetic variation in Soybean, *Theor. Appl. Genet.*, 95:220-225 (1997). Single Nucleotide Polymorphisms may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan et al, "An Integrated Genetic Linkage Map of the Soybean Genome," *Crop Science*, 39:1464-1490 (1999). Sequences and PCR conditions of SSR Loci in Soybean as well as the most current genetic map may be found in Soybase on the World Wide Web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

In another embodiment of the present invention, the invention relates to a soybean plant or seed with a heritable phenotype of: (i) an ultra-low raffinose seed content of less than 0.13% by dry or wet weight of the total seed content; (ii) an ultra-low stachyose seed content of less than 1.6% by dry or wet weight of the total seed content; and (iii) an seed germination rate of at least 83%.

In another embodiment, the present invention provides for methods for introducing the ultra-low raffinose and stachyose content phenotype of the present invention into plants by crossing a plant which lacks the ultra-low raffinose and stachyose content phenotype with a plant that exhibits the ultra-low raffinose and stachyose seed content and then selecting the plants exhibiting the ultra-low phenotype.

In another embodiment, the soybean seed of the present invention having and ultra-low raffinose and stachyose seed content can be utilized for human food, livestock feed, and as a raw material in industry. The soybean seed can be crushed or a component of the soybean seed can be extracted in order to comprise a component for a food or feed product.

Industrial uses of soybean oil which is subjected to further processing include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthier, less expensive replacement for animal protein in meats as well as in dairy-type products.

EXAMPLES

Introduction to Soybean Lines Williams 82 and PI 200508

Dierking and Bilyeu (*The Plant Genome*, 1(2): 135-145 (November 2008)) analyzed raffinose synthase genes: raffinose synthase 2 (RS2), raffinose synthase 3 (RS3) and raffinose synthase 4 (RS4) genes in a plant introduction line, PI 200508, that had been identified with having reduced levels of raffinose and stachyose and elevated levels of sucrose (Kerr and Sebastian (2000)). Soybean raffinose-synthase enzyme activity was investigated in the low raffinose and stachyose PI 200508, and in the wild-type control line, Williams 82.

Example 1

Discovery of the Original Mutant Plant Having an Ultra Low Raffinose and Stachyose Content The present invention arose from a mutation from a population of plants derived from PI 200508 in 2008. Two candidate lines, 247F and 222-18-1 exhibited reduced raffinose and stachyose seed content, based on the initial analysis of low raffinose and stachyose seed content. When the raffinose and stachyose seed levels were compared between the two lines, line 222-18-1 has a significantly and unexpectedly lower raffinose and stachyose seed content and was selected for further analysis.

Of the two candidate lines, 222-18-1 exhibited an ultra-low level of raffinose and stachyose seed content. The SG-UL-RFO mutant allele soybean seed is characterized by an ultra-low raffinose and stachyose seed content and high germination rates not characterized in soybean seeds before.

Introgression of the SG-ULRFO Mutant Allele into Different Genetic Backgrounds

The single mutant plant, 222-18-1 containing the SG-UL-RFO mutant allele of the present invention, was self-pollinated and the progeny were sown in 2008. The mutant plant 222-18-1 containing the SG-ULRFO mutant allele of the present invention was also crossed with different soybean genetic backgrounds and progeny seeds were sown and grown under controlled greenhouse and field conditions. An example of the progeny produced is shown in Table 1, where the soybean lines of the present invention exhibited the ultra-low raffinose and stachyose seed content and high germination rates.

Previously, lines with low raffinose and stachyose were thought to have poor germination. In order to quantify the ultra-low levels of raffinose and stachyose seed content, soybean lines were analyzed according to the protocol listed in Example 2. Germination rates were analyzed according to the protocol listed in Example 3.

Example 2

Analysis of Oligosaccharide Profiles Using HPLC

Soybean seed samples were ground with a Stein Mill. Sample preparation and extraction was as follows. Five grams of each sample was weighed and transferred to a 500 mL volumetric flask, to which about 250 mL deionized water was added. The flask was placed on a hot plate and brought to a boil. The mixture was let to cool to room temperature and the flask was brought to volume with deionized water and mixed. Five millilitres was taken from the flask and transferred to a 25 mL volumetric flask. The 25 mL flask was filled to volume with deionized water and mixed and 0.75 mL of this extract was filtered out into an HPLC autosampler vial using a 0.45 micron syringe filter and readings were taken. The HPLC System used was: Mobile Phase (0.1 N NaOH in DI/RO water), HPLC Pump (Waters 510, flow 1.0 mL/min), HPLC Autosampler (Micromeritics 728, injection volume 30 µL), HPLC Detector: Dionex PAD-2 (pulsed amperometric detector), HPLC Column (Dionex Carbopac PA-1), and HPLC Column Heater (50° C.). Methods of using HPLC are well-known to the person skilled in the art.

Example 3

Analysis Germination Rates in Warm and Cold Temperatures

Soybean seed germination rates were testing in warm and cold temperatures according the following protocols.

Protocol for Testing Germination of Seeds in Warm Temperatures

Soybean seeds were placed a single (18 ply) sheet of Versa-Pak (KimPak) or similar creped cellulose paper media on a germination tray. 500 ml±50 ml of water was added to the tray using the automatic tray waterer at the setting specified for soybean warm test (see, AOSA Rules for Testing Seed, AOSA Seedling Evaluation Handbook, and AOSA Seed Vigor Testing Handbook). The water was evenly distributed across the media with no dry areas. Approximately 500 ml of water was added to an empty germination tray in the bottom rack of the germination cart to maintain humidity in the cart. Four replicates of exactly 100 seeds each were placed on the Versa-Pak using seed counting boards. At least one sample identification tag was placed on each tray for each sample. The tray in a germination cart was placed leaving one empty tray rack between each sample tray to allow for hypocotyl elongation. When the cart was full, it was ensured that the bottom tray was watered. The identification numbers of the samples in the cart were recorded on a color-coded card and the read date was also recorded on the card; this information was attached to the back exterior of the cart so that the numbers were legible from the outside. The sample identification numbers were recorded on the wall calendar on the read date (seven days from planting date). For example, if seed is planted on November 10, the samples would be recorded on the calendar in the November 17 space. The door of the cart was closed and latched and placed in the germination chamber at 25° C.±1° C., normally for seven days. Reading early was allowable if deemed the sample had achieved maximum germination potential. The cart was removed from the chamber and evaluated according to the current version of the AOSA Rules for Testing Seed and the AOSA Seedling Evaluation Handbook. Results were recorded and submitted to Tags & Records for data entry.

Protocol for Testing Germination of Seeds in Cold Temperatures

Soybean seeds were placed a single (18 ply) sheet of Versa-Pak (KimPak) or similar creped cellulose paper media on a germination tray. 750±50 ml of water was added to the tray using the automatic tray waterer at the setting specified for soybean cold test (see, AOSA Rules for Testing Seed, AOSA Seedling Evaluation Handbook, and AOSA Seed Vigor Testing Handbook). The water was evenly distributed across the media with no dry areas. Approximately 500 ml of water was added to an empty germination tray in the bottom rack of the germination cart to maintain humidity. One replicate of exactly 100 seeds each was placed on the Versa-Pak using seed counting boards. A sample identification tag was placed with each replica of seed on the trays. Each sample was covered with approximately ⅛" of soil. The tray was placed in a germination cart leaving one empty tray rack between each sample tray to allow for hypocotyl elongation. When the cart was full, or when no additional samples were to be planted, it was ensured that the bottom tray was watered. The identification numbers of the samples contained in the cart were recorded onto a color-coded label/card with information such as planting date, transfer date and read date, which were included on the card. This information was attached to the back exterior of the cart so that the numbers were legible from the outside. The sample identification numbers were recorded on the wall calendar on the read date (eleven days from planting date). For example, if seed was planted on November 10, the samples would be recorded on the calendar in the November 21 space. The door of the cart was latched and closed and placed in the cold germination chamber at 10°±1° C., normally for seven days. The cart was removed from the cold chamber and place it in the warm 25°±1° C. chamber for four days. Reading early was allowable if deemed the sample to have achieved maximum germination potential. The cart was removed from the chamber and evaluated according to the current version of the AOSA Rules for Testing Seed and the AOSA Seedling Evaluation Handbook.

Example 4

Comparison of Sucrose, Raffinose and Stachyose Content in Soybean Seed from the Present Invention with Comparison Checks for Data Collected in 2008 in Argentina and the United States In Table 1, the sucrose, raffinose and stachyose seed content and the combined raffinose and stachyose content from seed derived from proprietary soybean lines having soybean 222-18-1 in their pedigree are compared to a check (control) line designated 388.TC. Column 1 shows the line, columns 2-5 show the sugar profile data collected in April 2008 in Argentina, column 2 shows the sucrose content, column 3 shows the raffinose content, column 4 shows stachyose content, column 5 shows the combined raffinose and stachyose content, columns 6-9 show the sugar profile data collected in October 2008 in the United States, column 6 shows the sucrose content, column 7 shows the raffinose content, column 8 shows the stachyose content, and column 9 shows the raffinose and stachyose content. Sucrose, raffinose and stachyose content are measured as percentage of dry weight of the seed content. Data were collected in April 2008 in Argentina and in October 2008 in the United States for comparison and to minimize environmental differences. The soybean seed containing 222-18-1 in their pedigree had significantly lower raffinose content, stachyose content and combined raffinose and stachyose content, while having a higher sucrose content when compared to the soybean check 388.TC that does not exhibit the ultra-low raffinose and stachyose phenotype. The combined raffinose and stachyose content of soybean plants of the present invention ranged from 0.27% to 1.75%, while the combined raffinose and stachyose content of 388.TC was an average of 4.77%. Thus, the soybean lines of the present invention have a reduced raffinose and stachyose content of about 2.73 to 17.67 times less than the check variety.

TABLE 1

| | April 2008-AR | | | | October 2008-US | | | |
| --- | --- | --- | --- | --- | --- | --- | --- | --- |
| Line | Sucrose | R | S | R + S | Sucrose | R | S | R + S |
| 928D120 | 6.2 | 0.03 | 0.33 | 0.36 | 7.0 | 0.04 | 0.39 | 0.43 |
| 932D129 | 3.1 | 0.00 | 0.19 | 0.19 | 7.1 | 0.05 | 0.39 | 0.44 |
| 932D130 | 7.8 | 0.04 | 0.38 | 0.42 | 8.0 | 0.03 | 0.32 | 0.35 |

TABLE 1-continued

| | April 2008-AR | | | | October 2008-US | | | |
| --- | --- | --- | --- | --- | --- | --- | --- | --- |
| Line | Sucrose | R | S | R + S | Sucrose | R | S | R + S |
| 926D108K | 5.1 | 0.05 | 1.04 | 1.09 | 7.1 | 0.09 | 1.09 | 1.18 |
| 222-18-1 | 7.5 | 0.13 | 0.58 | 0.71 | 7.1 | 0.05 | 0.37 | 0.42 |
| 928D119 | 3.6 | 0.03 | 0.60 | 0.63 | 6.0 | 0.15 | 1.60 | 1.75 |
| 931D125 | 6.3 | 0.00 | 0.27 | 0.27 | 8.1 | 0.03 | 1.33 | 0.36 |
| 933D132 | 5.8 | 0.10 | 1.10 | 1.20 | 7.3 | 0.08 | 1.06 | 1.14 |
| 934D201 | 5.5 | 0.06 | 0.71 | 0.77 | 5.6 | 0.13 | 1.25 | 1.38 |
| 936D205 | 2.3 | 0.03 | 0.32 | 0.35 | 5.6 | 0.13 | 1.25 | 1.38 |
| 938D211A | 2.8 | 0.06 | 0.77 | 0.83 | 5.5 | 0.14 | 1.29 | 1.43 |
| 939D214A | 5.4 | 0.08 | 0.94 | 1.02 | 5.2 | 0.11 | 1.00 | 1.11 |
| 941D221A | 5.4 | 0.07 | 0.84 | 0.91 | 5.0 | 0.15 | 1.15 | 1.30 |
| 388.TC | | | | | 4.4 | 0.97 | 3.8 | 4.77 |

Example 5

Figure 4:
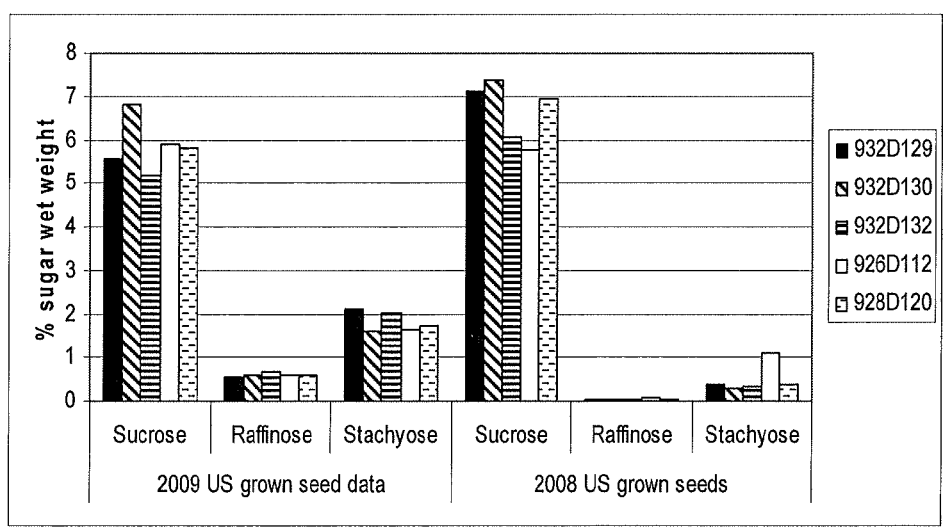
FIG. 4 compares sucrose, raffinose and stachyose content of soybean seed for the five advanced ultra-low raffinose and stachyose lines of the present invention over two different growing environments/seasons. The lines were grown first in the United States in 2008 and 2009. 932D129, 932D130 and 932D132 represent soybean lines with early three maturities and 926D112 and 928D120 represent soybean lines with late two maturities.

Comparison of Sucrose, Raffinose and Stachyose Content in Soybean Seed from the Present Invention in 2008 and 2009 from the United States In FIG. 4, the three oligosaccharides, sucrose, raffinose and stachyose content are analyzed in the five advanced ultra-low raffinose and stachyose lines over two different growing environments/seasons. The lines were grown first in the United States in 2008 and then advanced in Argentina over the winter of 2008. 932D129, 932D130, and 932D132 represent soybean lines with early three maturities and 926D112 and 928D120 represent soybean lines with late two maturities. The level of the raffinose and stachyose is very stable across environment and season. These lines also exhibit a significant reduction in raffinose and stachyose compared to the standard released varieties.

Example 6

Comparison of Sucrose, Raffinose and Stachyose Content and Germination Rates in Soybean Seed from the Present Invention with Comparison Checks in 2009 in the United States Table 2, the sucrose, raffinose and stachyose content and germination rates (in both warm and cold temperatures) is compared with the ultra-low raffinose and stachyose seed content soybean lines of the present invention with the check (control) lines (285.HPC and 348.TC) having normal raffinose and stachyose seed content. Soybean lines of the present invention, 926D112 and 928D120 share a late two maturity with the check variety 258F.HPC, while soybean lines of the present invention, 932D129, 932D130, and 933D132 share early three maturities with the check variety 348.TC. Column 1 shows the line, column 2 shows the sucrose content, column 3 shows the raffinose content, column 4 shows the stachyose content, column 5 shows the raffinose and stachyose content, and columns 6 and 7 show the germination rates in warm and cold temperatures, respectively.

The sucrose, raffinose and stachyose profiles were taken using HPLC. Previously, lines with low raffinose and stachyose were thought to have poor germination. Table 2 shows that an ultra-low raffinose and stachyose phenotype can be achieved with no significant reduction in germination as compared to a check lines. The data were taken from 2009 summer in the United States season and shows that a significant reduction in raffinose and stachyose in advanced lines of the present invention as compared to check varieties with similar maturities does not result in a significant reduction in germination.

TABLE 2

| Line | % sugar (dry weight) | | | | % Germination | |
| --- | --- | --- | --- | --- | --- | --- |
| | Sucrose | Raffinose | Stachyose | Raffinose + Stachyose | Warm | Cold |
| 926D112 | 7.85 | 0.06 | 0.46 | 0.52 | 99 | 86 |
| 928D120 | 7.94 | 0.06 | 0.62 | 0.68 | 99 | 90 |
| 258F.HPC | 5.30 | 0.94 | 4.35 | 5.29 | 99 | 95 |
| 932D129 | 6.04 | 0.00 | 0.52 | 0.52 | 84 | 83 |
| 932D130 | 6.68 | 0.06 | 0.67 | 0.73 | 93 | 92 |
| 933D132 | 6.27 | 0.09 | 1.78 | 1.87 | 96 | 89 |
| 348.TC | 5.08 | 0.67 | 4.94 | 5.61 | 97 | 95 |

Example 7

Figure 5:
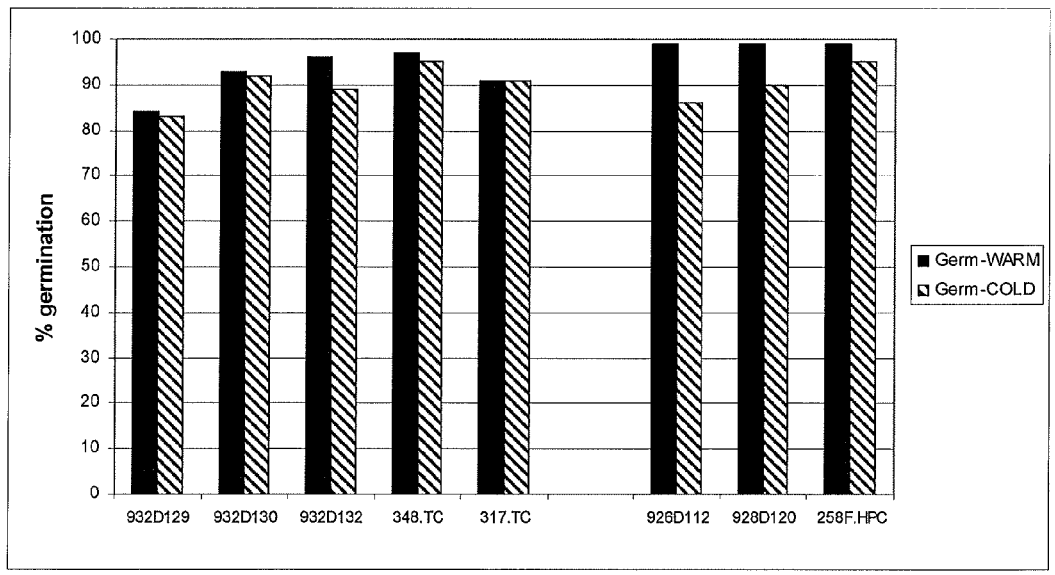
FIG. 5 compares the germination rates for the advanced ultra-low raffinose and stachyose lines of the present invention as compared to check lines with appropriate maturities. Each line was tested for germination in warm and cold temperatures. The seeds to create this data were produced in a 2009 United States growing season. The first five pairs of bars share an early three maturity. The first three pairs have ultra-low raffinose and stachyose phenotypes and the last two represent check (control) lines. The last three pairs or bars share late two maturities; the first two pairs have ultra-low raffinose and stachyose phenotypes and the last pair represents a check line.

Comparison of Germination Rates Between Soybean Seed of the Present Invention and Comparison Checks FIG. 5 compares the germination data for the advanced ultra-low raffinose and stachyose lines of the present invention as compared to check (control) lines with appropriate maturities. Each line was tested for germination in warm and cold temperatures. The seeds to create this data were produced in a 2009 US growing season. The first five pairs of bars share an early three maturity. The first three pairs have the low RFO phenotypes and the last two represent check lines. The last three pairs or bars share late two maturities; the first two pairs have low raffinose and stachyose seed contents and the last pair represents check (control) lines. As shown in FIG. 5, unexpectedly there are no significant differences in germination for an ultra-low raffinose and stachyose line of the present invention as compared to a check line with conventional levels of raffinose and stachyose.

Figure 6:
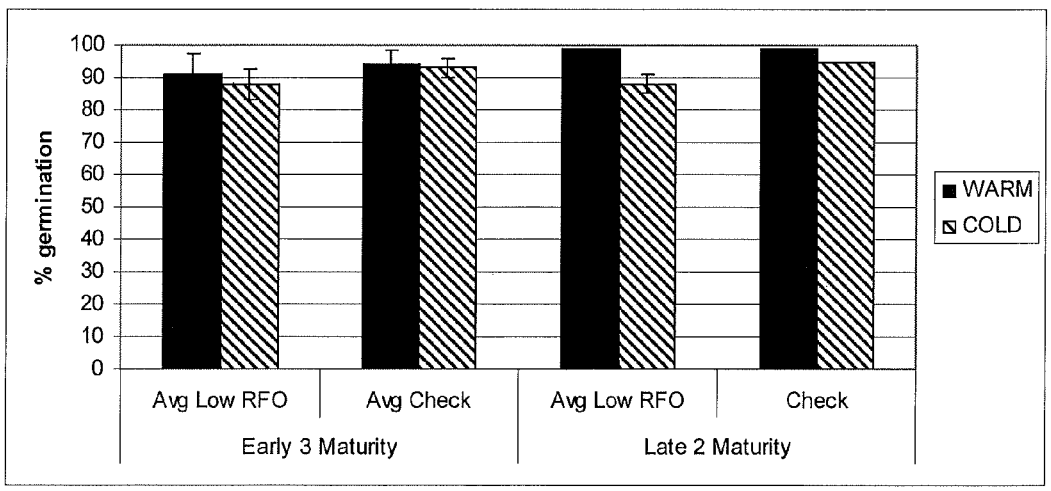
FIG. 6 displays the average germination rates for the advanced ultra-low raffinose and stachyose lines as compared to the average germination rates for the check (control) lines with similar maturities. Germination was tested in warm and cold temperatures and measured as the percent of the seeds that germinated for that line.

FIG. 6 displays the average germination for the advanced ultra-low raffinose and stachyose lines as compared to the average germination for the check lines with similar maturities. Germination was tested for in warm and cold temperatures. Germination is measured as a percent. As shown in FIG. 6, unexpectedly there are no significant differences in germination for an ultra low raffinose and stachyose line of the present invention as compared to a check line with conventional levels of these oligosaccharides.

Example 8

Identification of Polymorphisms in the RS3 and RS4 Raffinose Synthases and Association of the Mutant RS3 and RS4 Genes to the Ultra-Low Raffinose and Stachyose Phenotype In order to determine the genetic elements responsible for the ultra-low raffinose and stachyose seed content and the high germination rates, a molecular approach with soybean raffinose synthases as candidate genes was utilized.

The PI 200508 is a soybean line that was associated with low raffinose and stachyose seed content. The PI 200508 line is known to have an RS2 gene that was thought to confer a low raffinose and stachyose content. Dierking and Bilyeu, *The Plant Genome*, 1(2): 135-145 (November 2008). Due to the common RS2 sequence between the PI 200508 and 247F low raffinose and stachyose lines it is obvious that this gene is required for the low raffinose and stachyose phenotype. However, the unique ultra-low raffinose and stachyose phenotype observed in 222-18-1 must be due to the action of additional raffinose synthase genes in soybean. The remaining candidate genes RS3 and RS4 have been characterized for nucleotide difference between lines with low raffinose and stachyose phenotype (PI 200508 and 247F) and a line with ultra-low raffinose and stachyose phenotype (222-18-1). RS3 was amplified by PCR and sequenced as described. Dierking and Bilyeu, *The Plant Genome*, 1(2): 135-145 (November 2008). The RS4 gene was discovered after the release of the soybean genome sequence due to its homology to soybean, pea and *Arabidopsis* raffinose synthase genes. This gene was amplified by gene specific primers and sequenced from Williams 82, PI 200508, 247F and 222-18-1. The RS3 and RS4 genes which are unique to the ultra low raffinose and stachyose line 222-18-1 were first identified using the primers as disclosed in SEQ ID NO:8 to SEQ. ID NO:18. Polymorphisms in the RS3 and RS4 genes were then identified using a set of primers for each separate exon. These unique polymorphisms result in amino acid changes and confer the ultra-low raffinose and stachyose phenotype.

For the mutant RS3 sequence, four polymorphisms exist in the 222-18-1, RS3 sequence when compared to the 247F (247F and Williams 82 are identical for RS3) sequence. Two of these polymorphisms are silent and thus do not result in amino acid changes. Of the remaining two, one occurs in exon one, and the second in exon 2. The exon 1 polymorphism is a proline to alanine amino acid change (C28G; P10A). The exon 2 polymorphism is an arginine to glycine amino acid change (C1105G; R369G).

For the mutant RS4 sequence from 222-18-1, it is unique containing three mutations as compared to wild-type sequence (Williams 82, PI 200508, and 247F sequences are all identical for the RS4 gene). The novel sequence contains three polymorphisms, one in exon one and a second and third in exon two. The exon one polymorphism is silent, while one of the exon two polymorphisms is silent and one results in an amino acid change from glutamic acid to a glycine residue (A1061G;E354G).

DEPOSIT INFORMATION

A deposit of the Schillinger Genetics, Inc. proprietary soybean seed disclosed above and recited in the appended claims has been made with American. Type Culture Collection, 10801 University Boulevard, Manassas,V.A. 20110. The date of deposit was Apr. 16, 2010. The deposit of 2,500 seeds was taken from the same deposit maintained by Schillinger Genetics, Inc. since prior to the filing date of this application. All restrictions will be removed upon granting of a patent, and the deposit is intended to meet all of the requirements 37 C.F.R. §§1.801-1.809. The deposit number is PTA-10830. The deposit will be maintained in the depository for a period of thirty years, or five years after the last request, or for the enforceable life of the patent, whichever is longer, and will be replaced as necessary during the period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

What is claimed is:

1. A soybean seed, wherein the soybean seed comprises an RS2 mutant allele, and RS3 mutant allele and an RS4 mutant allele and, wherein a representative sample of seed has been deposited with ATCC Accession No. PTA-10830.

2. A soybean plant or a part thereof, produced by growing the seed of claim 1.

3. The soybean seed of claim 1, wherein the germination rate is at least 83%.

4. A isolated nucleic acid sequence as set forth in SEQ ID NO:5.

5. A soybean seed comprising a nucleic acid sequence encoding an RS2 polypeptide having the amino acid sequence as set forth in SEQ ID NO:2, a nucleic acid sequence encoding an RS3 polypeptide having the amino acid sequence as set forth in SEQ ID NO:4 and a nucleic acid sequence encoding an RS4 polypeptide having the amino acid sequence as set forth in SEQ ID NO:6.

6. A soybean plant, or a part thereof, produced by growing the seed of claim 5.

7. A vector comprising the nucleic acid sequence of SEQ ID NO:1, the nucleic acid sequence of SEQ ID NO:3 and the nucleic acid sequence of SEQ ID NO:5.

8. A method of producing a commodity plant product, comprising obtaining the plant of claim 2, or a part thereof, wherein the commodity plant product is protein concentrate, protein isolate, soybean hulls, meal, flour or oil and producing said commodity plant product therefrom.

* * * * *

SEQUENCE LISTING

<160> NUMBER OF SEQ ID NOS: 18

<210> SEQ ID NO 1
<211> LENGTH: 2346
<212> TYPE: DNA
<213> ORGANISM: Glycine max

<400> SEQUENCE: 1

```
atggctccaa gcataagcaa aactgtggaa ctaaattcat ttggtcttgt caacggtaat      60
ttgcctttgt ccataaccct agaaggatca aatttcctcg ccaacggcca ccctttctc     120
acggaagttc ccgaaaacat aatagtcacc ccttcaccca tcgacgccaa gagtagtaag    180
aacaacgagg acgacgacgt cgtaggttgc ttcgtgggct ccacgcggaa cgagcccaga    240
agccgacacg tggcttccct ggggaagctc agaggaataa aattcatgag catattccgg    300
tttaaggtgt ggtggaccac tcactgggtc ggtagcaacg acacgaact ggagcacgag     360
acacagatga tgcttctcga caaaaacgac cagctcggac gccccttgt gttgattctc      420
ccgatcctcc aagcctcgtt ccgagcctcc ctgcaacccg gtttgatga ttacgtggac      480
gtttgcatgg agagcgggtc gacacgtgtc tgtggctcca gcttcgggag ctgcttatac    540
gtccacgttg ccatgacccc gtatcagttg cttagagaag caactaaagt cgttaggatg    600
catttgggga cgttcaagct tctcgaggag aaaaccgcgc cagtgatcat agacaagttt    660
ggttggtgta catgggacgc gttttacttg aaggtgcatc cctcaggtgt gtgggaaggg    720
gtgaaagggt tggtggaggg agggtgccct ccagggatgg tcctaatcga cgacgggtgg    780
caagccattt gtcacgacga ggaccccata acggaccaag agggtatgaa gcgaacctcc    840
gcagggagc aaatgccatg caggttggtg aagttggagg aaaattacaa gttcagacag     900
tattgtagtg gaaaggattc tgagaagggt atgggtgcct tgttaggga cttgaaggaa     960
cagtttagga gcgtggagca ggtgtatgtg tggcacgcgc tttgtgggta ttggggtggg   1020
gtcagaccca aggttccggg catgccccag gctaaggttg tcactccgaa gctgtccaat   1080
ggactaaaat tgacaatgaa ggatttagcg gtggataaga tcgtcagtaa cggagttgaa   1140
ctggtgccac cacacctggc tcaccttttg tacgaagggc tccactcccg tttggaatct   1200
gcgggtattg acggtgttaa ggttgacgtt atacacttgc tcgagatgct atccgaggaa   1260
tacggtggcc gtgttgagct agccaaagct tattacaaag cgctcactgc ttcggtgaag   1320
aagcatttca aaggcaatgg ggtcattgcg agcatggagc attgtaatga cttctttctc   1380
cttggtaccg aagccatagc ccttgggcgc gtaggagatg attttggtg cactgatccc    1440
tctgagatc caaatggcac gtattggctc caagggtgtc acatggtgca ctgtgcctac   1500
aacagcttgt ggatggggaa ttttattcag ccggattggg acatgttcca gtccactcac   1560
ccttgtgccg aattccatgc agcctctagg gccatctctg gtggaccagt ttacgttagt   1620
gattgtgttg gaaagcacaa cttcaagttg ctcaagagcc tcgctttgcc tgatgggacg   1680
attttgcgtt gtcaacacta tgcactcccc acacgagact gtttgtttga agaccccttg   1740
catgatggga agacaatgct caaaatttgg aatctcaaca aatatacagg tgttttgggt   1800
ctatttaatt gccaaggagg tgggtggtgt cccgtaacta ggagaaacaa gagtgcctct   1860
gaattttcac aaactgtgac atgcttagcg agtcctcaag acattgaatg gagcaatggg   1920
aaaagcccaa tatgcataaa agggatgaat gtgtttgctg tatatttgtt caaggaccac   1980
aaactaaagc tcatgaaggc atcagagaaa ttggaagttt cacttgagcc atttactttt   2040
```

```
gagctattga cagtgtctcc agtgattgtg ctgtcaaaaa agttaattca atttgctcca    2100
attggattag tgaacatgct taacactggt ggtgccattc agtccatgga gtttgacaac    2160
cacatagatg tggtcaaaat tggggttagg ggttgtgggg agatgaaggt gtttgcatca    2220
gagaaaccag ttagttgcaa actagatggg gtagttgtaa aatttgatta tgaggataaa    2280
atgctgagag tgcaagttcc ctggcctagt gcttcaaaat tgtcaatggt tgagtttta    2340 ttttga                                                               2346

<210> SEQ ID NO 2
<211> LENGTH: 781
<212> TYPE: PRT
<213> ORGANISM: Glycine max

<400> SEQUENCE: 2

Met Ala Pro Ser Ile Ser Lys Thr Val Glu Leu Asn Ser Phe Gly Leu
1               5                   10                  15

Val Asn Gly Asn Leu Pro Leu Ser Ile Thr Leu Glu Gly Ser Asn Phe
            20                  25                  30

Leu Ala Asn Gly His Pro Phe Leu Thr Glu Val Pro Glu Asn Ile Ile
        35                  40                  45

Val Thr Pro Ser Pro Ile Asp Ala Lys Ser Ser Lys Asn Asn Glu Asp
    50                  55                  60

Asp Asp Val Val Gly Cys Phe Val Gly Phe His Ala Asp Glu Pro Arg
65                  70                  75                  80

Ser Arg His Val Ala Ser Leu Gly Lys Leu Arg Gly Ile Lys Phe Met
                85                  90                  95

Ser Ile Phe Arg Phe Lys Val Trp Trp Thr Thr His Trp Val Gly Ser
            100                 105                 110

Asn Gly His Glu Leu Glu His Glu Thr Gln Met Met Leu Leu Asp Lys
        115                 120                 125

Asn Asp Gln Leu Gly Arg Pro Phe Val Leu Ile Leu Pro Ile Leu Gln
    130                 135                 140

Ala Ser Phe Arg Ala Ser Leu Gln Pro Gly Leu Asp Asp Tyr Val Asp
145                 150                 155                 160

Val Cys Met Glu Ser Gly Ser Thr Arg Val Cys Gly Ser Ser Phe Gly
                165                 170                 175

Ser Cys Leu Tyr Val His Val Gly His Asp Pro Tyr Gln Leu Leu Arg
            180                 185                 190

Glu Ala Thr Lys Val Val Arg Met His Leu Gly Thr Phe Lys Leu Leu
        195                 200                 205

Glu Glu Lys Thr Ala Pro Val Ile Ile Asp Lys Phe Gly Trp Cys Thr
    210                 215                 220

Trp Asp Ala Phe Tyr Leu Lys Val His Pro Ser Gly Val Trp Glu Gly
225                 230                 235                 240

Val Lys Gly Leu Val Glu Gly Gly Cys Pro Pro Gly Met Val Leu Ile
                245                 250                 255

Asp Asp Gly Trp Gln Ala Ile Cys His Asp Glu Asp Pro Ile Thr Asp
            260                 265                 270

Gln Glu Gly Met Lys Arg Thr Ser Ala Gly Glu Gln Met Pro Cys Arg
        275                 280                 285

Leu Val Lys Leu Glu Glu Asn Tyr Lys Phe Arg Gln Tyr Cys Ser Gly
    290                 295                 300

Lys Asp Ser Glu Lys Gly Met Gly Ala Phe Val Arg Asp Leu Lys Glu
305                 310                 315                 320
```

-continued

```
Gln Phe Arg Ser Val Glu Gln Val Tyr Val Trp His Ala Leu Cys Gly
                325                 330                 335
Tyr Trp Gly Gly Val Arg Pro Lys Val Pro Gly Met Pro Gln Ala Lys
            340                 345                 350
Val Val Thr Pro Lys Leu Ser Asn Gly Leu Lys Leu Thr Met Lys Asp
        355                 360                 365
Leu Ala Val Asp Lys Ile Val Ser Asn Gly Val Gly Leu Val Pro Pro
    370                 375                 380
His Leu Ala His Leu Leu Tyr Glu Gly Leu His Ser Arg Leu Glu Ser
385                 390                 395                 400
Ala Gly Ile Asp Gly Val Lys Val Asp Val Ile His Leu Leu Glu Met
            405                 410                 415
Leu Ser Glu Glu Tyr Gly Gly Arg Val Glu Leu Ala Lys Ala Tyr Tyr
        420                 425                 430
Lys Ala Leu Thr Ala Ser Val Lys Lys His Phe Lys Gly Asn Gly Val
    435                 440                 445
Ile Ala Ser Met Glu His Cys Asn Asp Phe Phe Leu Leu Gly Thr Glu
    450                 455                 460
Ala Ile Ala Leu Gly Arg Val Gly Asp Asp Phe Trp Cys Thr Asp Pro
465                 470                 475                 480
Ser Gly Asp Pro Asn Gly Thr Tyr Trp Leu Gln Gly Cys His Met Val
            485                 490                 495
His Cys Ala Tyr Asn Ser Leu Trp Met Gly Asn Phe Ile Gln Pro Asp
        500                 505                 510
Trp Asp Met Phe Gln Ser Thr His Pro Cys Ala Glu Phe His Ala Ala
    515                 520                 525
Ser Arg Ala Ile Ser Gly Gly Pro Val Tyr Val Ser Asp Cys Val Gly
    530                 535                 540
Lys His Asn Phe Lys Leu Leu Lys Ser Leu Ala Leu Pro Asp Gly Thr
545                 550                 555                 560
Ile Leu Arg Cys Gln His Tyr Ala Leu Pro Thr Arg Asp Cys Leu Phe
            565                 570                 575
Glu Asp Pro Leu His Asp Gly Lys Thr Met Leu Lys Ile Trp Asn Leu
        580                 585                 590
Asn Lys Tyr Thr Gly Val Leu Gly Leu Phe Asn Cys Gln Gly Gly Gly
    595                 600                 605
Trp Cys Pro Val Thr Arg Arg Asn Lys Ser Ala Ser Glu Phe Ser Gln
    610                 615                 620
Thr Val Thr Cys Leu Ala Ser Pro Gln Asp Ile Glu Trp Ser Asn Gly
625                 630                 635                 640
Lys Ser Pro Ile Cys Ile Lys Gly Met Asn Val Phe Ala Val Tyr Leu
            645                 650                 655
Phe Lys Asp His Lys Leu Lys Leu Met Lys Ala Ser Glu Lys Leu Glu
        660                 665                 670
Val Ser Leu Glu Pro Phe Thr Phe Glu Leu Leu Thr Val Ser Pro Val
    675                 680                 685
Ile Val Leu Ser Lys Lys Leu Ile Gln Phe Ala Pro Ile Gly Leu Val
    690                 695                 700
Asn Met Leu Asn Thr Gly Gly Ala Ile Gln Ser Met Glu Phe Asp Asn
705                 710                 715                 720
His Ile Asp Val Val Lys Ile Gly Val Arg Gly Cys Gly Glu Met Lys
            725                 730                 735
Val Phe Ala Ser Glu Lys Pro Val Ser Cys Lys Leu Asp Gly Val Val
        740                 745                 750
```

| Val | Lys | Phe | Asp | Tyr | Glu | Asp | Lys | Met | Leu | Arg | Val | Gln | Val | Pro | Trp |
|---|---|---|---|---|---|---|---|---|---|---|---|---|---|---|---|
| | | | | 755 | | | | 760 | | | | 765 | | | |

| Pro | Ser | Ala | Ser | Lys | Leu | Ser | Met | Val | Glu | Phe | Leu | Phe |
|---|---|---|---|---|---|---|---|---|---|---|---|---|
| 770 | | | | 775 | | | | 780 | | | | |

<210> SEQ ID NO 3
<211> LENGTH: 2277
<212> TYPE: DNA
<213> ORGANISM: Glycine max

<400> SEQUENCE: 3

```
atgggtccaa gctcgaagaa agcttcagct aaatcaggtg tgacaaagca catgaagggc      60
ttcagcctct gcaactcaac cctaaaagta aatgggcaag tcatcctctc ccaagtcccc     120
aagaacgtaa ccctcacccc atgcacctac gacactcaca ccaccggatg cttcctcggt     180
ttccacgcca cctccccaaa atcccgccac gtggcaccct taggacagct taaaaacata     240
agcttcactt ccatcttccg gttcaaggtt tggtggacca ctctctggac cggctccaac     300
ggccgcgacc tggaaaccga aacccaattc ctcatgctcc aatcccaccc ttatgttctc     360
ttcctaccca tcctccaacc cccatttcgc gcctcgctgc agcctcactc agacgacaac     420
gttgcggtgt gtgtggagag cggctccagc cacgtaacag cctcatcatt cgacactgtc     480
gtctacttgc acgcagggga caaccccttc acgctggtca aggaagccat gcgcgtcgtc     540
cgggcccact ggggagctt caagcttctg aagagaaaa cagttccggg aatggtggac      600
aagttcggtt ggtgcacgtg ggacgccttt tacctgacgg tgcaccctga gggcgtcaga     660
gagggcgtga agggcctggt tgacggcggt tgtcctccgg gattcgtcct gatcgacgac     720
ggctggcagt gcatcagcca cgattccgat ccggagaagg aggggatgaa tcagacggtg     780
gccggggagc aaatgccctg caggttgatt agttacgagg agaattacaa gtttaggagc     840
tataaggaag ggaaggggtt gaaggggttt gtgagagaat tgaaggagga gttgggtcg     900
gtggagtacg tgtacgtgtg gcacgcgctg tgcgggtatt ggggaggggt gaggccgggg     960
gtggcgggga tggcggaggc ggcggtggag aagccaaagc tgacggaggg gttgaaggga    1020
acgatggagg atctggcggt ggacaagatt gtgaataatg gggtcggggt ggtgccgccg    1080
gagctggtgg gggaaatgta tgagggcctt cacgcgcact tggagagtgc gggtattgat    1140
ggggtcaaag ttgatgtcat ccacttgcta gaaatggtgt gtgagaaata tggagggcga    1200
gtggatatgg cgaaagcata ttacaaagct ctcactgctt ccgtgagaaa acattttaag    1260
ggcaacggcg tcattgccag catggagcat tgcaacgatt tcatgttgct gggaactgaa    1320
gcaatatccc ttggtcgtgt tgggatgat ttctggtgca ctgacccttta tggtgatcca    1380
aatggtacat tttggctaca agggtgtcac atggtgcatt gtgcatacaa cagcttgtgg    1440
atgggcaatt tcatccaccc agattgggac atgttccaat ctactcatcc ttgtgctgcc    1500
ttccatgctg cctcaagagc catatctggt ggccccattt acatcagtga cagttgggg    1560
aaccacaact tgagctgct taagaccttg gccttgccag atgggtccat cctcagatgt    1620
gagcactatg cactcccaac caggggactgt ctctttgctg accctctcca tgatggcaaa    1680
acaatgctca agatatggaa cctcaacaag tacactggag ttcttggggt gtttaactgc    1740
cagggaggag gttggttccg tgagattagg tccaacaaat gtgctgctga gttttctcat    1800
agggtatcaa ccaagaccaa tatcaaagac attgaatggg atagtggaaa gaatccaatt    1860
tccattgaag gggtgcaact tttcgcttcg tatttcagcc aagccaagaa actcatcctc    1920
tcagcaccat ctgatgacag tgaagagatt tccttggagc cattcaattt cgagcttata    1980
```

```
acagtttccc ctgtgactgt cttgcctggc aagtcagtga agtttgctcc tattggtttg    2040
gtgaatatgc taaacactgg tggagcagtc cagtctttag cttttgatga gggtcagaat    2100
ttggttgaag ttggtttaag aggcactggg gagatgagag tctatgcctc agagaaacca    2160
agaacttgta gaattgatgg caaagaagtt gattttgaat atgaagggtc tatggtcaac    2220
attcaagtac catggcctgg ttcttcaaaa ttgtccactg ttcagtatgt attttaa       2277
```

<210> SEQ ID NO 4
<211> LENGTH: 758
<212> TYPE: PRT
<213> ORGANISM: Glycine max

<400> SEQUENCE: 4

```
Met Gly Pro Ser Ser Lys Lys Ala Ser Ala Lys Ser Gly Val Thr Lys
1               5                   10                  15

His Met Lys Gly Phe Ser Leu Cys Asn Ser Thr Leu Lys Val Asn Gly
            20                  25                  30

Gln Val Ile Leu Ser Gln Val Pro Lys Asn Val Thr Leu Thr Pro Cys
        35                  40                  45

Thr Tyr Asp Thr His Thr Thr Gly Cys Phe Leu Gly Phe His Ala Thr
    50                  55                  60

Ser Pro Lys Ser Arg His Val Ala Pro Leu Gly Gln Leu Lys Asn Ile
65                  70                  75                  80

Ser Phe Thr Ser Ile Phe Arg Phe Lys Val Trp Trp Thr Thr Leu Trp
                85                  90                  95

Thr Gly Ser Asn Gly Arg Asp Leu Glu Thr Glu Thr Gln Phe Leu Met
            100                 105                 110

Leu Gln Ser His Pro Tyr Val Leu Phe Leu Pro Ile Leu Gln Pro Pro
        115                 120                 125

Phe Arg Ala Ser Leu Gln Pro His Ser Asp Asp Asn Val Ala Val Cys
    130                 135                 140

Val Glu Ser Gly Ser Ser His Val Thr Ala Ser Ser Phe Asp Thr Val
145                 150                 155                 160

Val Tyr Leu His Ala Gly Asp Asn Pro Phe Thr Leu Val Lys Glu Ala
                165                 170                 175

Met Arg Val Val Arg Ala His Leu Gly Ser Phe Lys Leu Leu Glu Glu
            180                 185                 190

Lys Thr Val Pro Gly Met Val Asp Lys Phe Gly Trp Cys Thr Trp Asp
        195                 200                 205

Ala Phe Tyr Leu Thr Val His Pro Glu Gly Val Arg Glu Gly Val Lys
    210                 215                 220

Gly Leu Val Asp Gly Gly Cys Pro Pro Gly Phe Val Leu Ile Asp Asp
225                 230                 235                 240

Gly Trp Gln Cys Ile Ser His Asp Ser Asp Pro Glu Lys Glu Gly Met
                245                 250                 255

Asn Gln Thr Val Ala Gly Glu Gln Met Pro Cys Arg Leu Ile Ser Tyr
            260                 265                 270

Glu Glu Asn Tyr Lys Phe Arg Ser Tyr Lys Glu Lys Gly Leu Lys
        275                 280                 285

Gly Phe Val Arg Glu Leu Lys Glu Glu Phe Gly Ser Val Glu Tyr Val
    290                 295                 300

Tyr Val Trp His Ala Leu Cys Gly Tyr Trp Gly Gly Val Arg Pro Gly
305                 310                 315                 320

Val Ala Gly Met Ala Glu Ala Ala Val Glu Lys Pro Lys Leu Thr Glu
```

-continued

```
                325                 330                 335
Gly Leu Lys Gly Thr Met Glu Asp Leu Ala Val Asp Lys Ile Val Asn
            340                 345                 350
Asn Gly Val Gly Val Val Pro Pro Glu Leu Val Gly Glu Met Tyr Glu
            355                 360                 365
Gly Leu His Ala His Leu Glu Ser Ala Gly Ile Asp Gly Val Lys Val
            370                 375                 380
Asp Val Ile His Leu Leu Glu Met Val Cys Glu Lys Tyr Gly Gly Arg
385                 390                 395                 400
Val Asp Met Ala Lys Ala Tyr Tyr Lys Ala Leu Thr Ala Ser Val Arg
            405                 410                 415
Lys His Phe Lys Gly Asn Gly Val Ile Ala Ser Met Glu His Cys Asn
            420                 425                 430
Asp Phe Met Leu Leu Gly Thr Glu Ala Ile Ser Leu Gly Arg Val Gly
            435                 440                 445
Asp Asp Phe Trp Cys Thr Asp Pro Tyr Gly Asp Pro Asn Gly Thr Phe
            450                 455                 460
Trp Leu Gln Gly Cys His Met Val His Cys Ala Tyr Asn Ser Leu Trp
465                 470                 475                 480
Met Gly Asn Phe Ile His Pro Asp Trp Asp Met Phe Gln Ser Thr His
            485                 490                 495
Pro Cys Ala Ala Phe His Ala Ala Ser Arg Ala Ile Ser Gly Gly Pro
            500                 505                 510
Ile Tyr Ile Ser Asp Thr Val Gly Asn His Asn Phe Glu Leu Leu Lys
            515                 520                 525
Thr Leu Ala Leu Pro Asp Gly Ser Ile Leu Arg Cys Glu His Tyr Ala
            530                 535                 540
Leu Pro Thr Arg Asp Cys Leu Phe Ala Asp Pro Leu His Asp Gly Lys
545                 550                 555                 560
Thr Met Leu Lys Ile Trp Asn Leu Asn Lys Tyr Thr Gly Val Leu Gly
            565                 570                 575
Val Phe Asn Cys Gln Gly Gly Gly Trp Phe Arg Glu Ile Arg Ser Asn
            580                 585                 590
Lys Cys Ala Ala Glu Phe Ser His Arg Val Ser Thr Lys Thr Asn Ile
            595                 600                 605
Lys Asp Ile Glu Trp Asp Ser Gly Lys Asn Pro Ile Ser Ile Glu Gly
            610                 615                 620
Val Gln Leu Phe Ala Ser Tyr Phe Ser Gln Ala Lys Lys Leu Ile Leu
625                 630                 635                 640
Ser Ala Pro Ser Asp Asp Ser Glu Glu Ile Ser Leu Glu Pro Phe Asn
            645                 650                 655
Phe Glu Leu Ile Thr Val Ser Pro Val Thr Val Leu Pro Gly Lys Ser
            660                 665                 670
Val Lys Phe Ala Pro Ile Gly Leu Val Asn Met Leu Asn Thr Gly Gly
            675                 680                 685
Ala Val Gln Ser Leu Ala Phe Asp Glu Gly Gln Asn Leu Val Glu Val
            690                 695                 700
Gly Leu Arg Gly Thr Gly Glu Met Arg Val Tyr Ala Ser Glu Lys Pro
705                 710                 715                 720
Arg Thr Cys Arg Ile Asp Gly Lys Glu Val Asp Phe Glu Tyr Glu Gly
            725                 730                 735
Ser Met Val Asn Ile Gln Val Pro Trp Pro Gly Ser Ser Lys Leu Ser
            740                 745                 750
```

-continued

Thr Val Gln Tyr Val Phe
       755

<210> SEQ ID NO 5
<211> LENGTH: 2358
<212> TYPE: DNA
<213> ORGANISM: Glycine max
<220> FEATURE:
<221> NAME/KEY: misc_feature
<222> LOCATION: (1064)..(1064)
<223> OTHER INFORMATION: n is a, c, g, or t

<400> SEQUENCE: 5

| | | | | | |
|---|---|---|---|---|---|
| atggcgccaa | gcctaaccgc | caagcaagaa | gcggcgcttc | tcaacgcaaa | tccacactta | 60 |
| tccataaaac | tccaatcctc | aactttcttc | gctaacaacc | acccaatcct | cacccaagtc | 120 |
| ccaccgaaca | taacaacaac | cactccaccg | ccccacgatg | cttccaccac | cccgccgga | 180 |
| tgcttcgtcg | gtttctccgc | cgacgaggca | cgcagccggc | acgtgatctc | cctcggcaaa | 240 |
| ctgagggta | tcagattcac | gagcattttc | cgcttcaagc | tctggtggag | cacccactgg | 300 |
| tccggcagca | acggccgcga | cgtggagaac | gaaacccaaa | tgatgatcct | ccaaaacgac | 360 |
| gccgtcgagg | gccgacccta | cgtcctcctc | ctcccactcc | tcgaaggacc | cttccgagcc | 420 |
| tcgctccaac | ccggcctcca | cgacgacgtg | gacatctgca | tggagagcgg | ctccgcacgt | 480 |
| gtcaccaagt | cacgcttccg | aacctccgtc | tacatgcacg | tgcacgacga | tccttttact | 540 |
| ctaatcgacg | aagcgctgaa | agtaatccga | gtctatctcg | gaacgtttag | gttaatggaa | 600 |
| gagaaaccg | tgccggggat | tattgacaag | ttcgggtggt | gcacgtggga | cgcgttttac | 660 |
| cttaacgtgc | acccggaggg | ggtgcgggaa | ggaattaagg | gcctggtgga | gggagggtgt | 720 |
| cctccggggt | tggtactgat | cgacgacggt | tggcaaacat | tttgccgtga | cgacgaaacc | 780 |
| gtgagcgacg | gggggagttt | aaattgctct | gtgccggggg | agcagatgct | gaataggttg | 840 |
| ataaaatttg | aagagaatgg | caagtttaag | gagtataagt | gtgggaggga | gggtaataag | 900 |
| ggtatgggtg | cgtttgtgag | ggagttgaag | gaggaattta | gtgggttgga | gtatgtatat | 960 |
| gtgtggcatg | cgtttttgtgg | gtactgggga | ggggttaggc | ctaaggtgcc | ggggatgccg | 1020 |
| gaggccacgg | tggttccgac | caagttgtct | cccggagcgg | ggangactat | gacggaccag | 1080 |
| gcggtggtga | agatcatgga | gattggggtg | gggttggtgc | caccgcatcg | ggcgcatgag | 1140 |
| ttgtacgagg | ggcttcactc | tcatctggaa | tcggtgggaa | ttgatggtgt | caagattgat | 1200 |
| gtcacgcata | ttctagagat | gctatccgag | gaatatggtg | gtcgtgtcga | actcgctaaa | 1260 |
| gcatattaca | aagcactcac | tgcttccgtg | aggaagcatt | tcaaaggcaa | tggtgtcatt | 1320 |
| tcaagcatgc | agcagtgcaa | tgatttcatg | ttccttggta | cggaaaccat | atcacttgga | 1380 |
| cgagtcgatt | cattccataa | atgtgagttg | tggtacattc | atgcaggtga | tgatttttgg | 1440 |
| tgcacggacc | cagctggaga | tccaaaacggt | acctattggc | tgcaagggtg | tcacatggtg | 1500 |
| cactgtgctt | acaacagctt | gtggatggga | aatttcatac | cccagattg | ggacatgttc | 1560 |
| caatctgatc | atgcttgtgc | cgaattccac | gctgcttcta | gagccatttc | tggtggacca | 1620 |
| atttatgtaa | gcgactctgt | tggaaaacac | aacttcaagt | tgcttaagaa | gcttgttcta | 1680 |
| cctgatggct | ccattttgcg | gtgtcaacat | tatgcacttc | ccaccgaga | ctgcttattt | 1740 |
| gtagatcctt | tacatgatgg | gaaaacaatg | ctcaaaattt | ggaacctcaa | taatgttcc | 1800 |
| ggggttttgg | gtctgttcaa | ttgccaagga | ggaggttggt | gccctgttac | taggcgaaac | 1860 |
| aagagtagct | ctgactattc | acactccgtg | acttgctttg | caagtcctca | agacattgaa | 1920 |
| tggggcaaag | ggaagcaccc | agtttgcatc | aaaggggtgg | acgtatttgc | tgtgtacatg | 1980 |

-continued

```
tttaaggacg acaagttgaa gctgctgaag tacacagaga gtgtagaagt ttctcttgag    2040
ccttttagtt gtgagctttt gaccgtttct ccagtggtga tcttacccag aaaatcaatc    2100
caatttgccc caattggatt ggtaaacatg ctcaactctg ggggctctat tatgtcattg    2160
gaatttgatc aacaggaaaa tttggcgagg attggggtga gaggacatgg ggaaatgagg    2220
gtatttgcat cagagaagcc agagagtgtc aagattgatg agaatctgt ggaatttgat     2280 tatgttgata gaaccgtgag gctccaagtc tcgtggcctt gttcttcgag gttgtccgta    2340
gtcgagtatt tgttctga                                                   2358
```

```
<210> SEQ ID NO 6
<211> LENGTH: 785
<212> TYPE: PRT
<213> ORGANISM: Glycine max
<220> FEATURE:
<221> NAME/KEY: misc_feature
<222> LOCATION: (355)..(355)
<223> OTHER INFORMATION: The 'Xaa' at location 355 stands for Lys, Arg,
      Thr, or Met.

<400> SEQUENCE: 6
```

```
Met Ala Pro Ser Leu Thr Ala Lys Gln Glu Ala Ala Leu Leu Asn Ala
1               5                   10                  15

Asn Pro His Leu Ser Ile Lys Leu Gln Ser Ser Thr Phe Phe Ala Asn
            20                  25                  30

Asn His Pro Ile Leu Thr Gln Val Pro Pro Asn Ile Thr Thr Thr Thr
        35                  40                  45

Pro Pro Pro His Asp Ala Ser Thr Thr Pro Ala Gly Cys Phe Val Gly
    50                  55                  60

Phe Ser Ala Asp Glu Ala Arg Ser Arg His Val Ile Ser Leu Gly Lys
65                  70                  75                  80

Leu Arg Gly Ile Arg Phe Thr Ser Ile Phe Arg Phe Lys Leu Trp Trp
                85                  90                  95

Ser Thr His Trp Ser Gly Ser Asn Gly Arg Asp Val Glu Asn Glu Thr
            100                 105                 110

Gln Met Met Ile Leu Gln Asn Asp Ala Val Glu Gly Arg Pro Tyr Val
        115                 120                 125

Leu Leu Leu Pro Leu Leu Glu Gly Pro Phe Arg Ala Ser Leu Gln Pro
    130                 135                 140

Gly Leu His Asp Asp Val Asp Ile Cys Met Glu Ser Gly Ser Ala Arg
145                 150                 155                 160

Val Thr Lys Ser Arg Phe Arg Thr Ser Val Tyr Met His Val His Asp
                165                 170                 175

Asp Pro Phe Thr Leu Ile Asp Glu Ala Leu Lys Val Ile Arg Val Tyr
            180                 185                 190

Leu Gly Thr Phe Arg Leu Met Glu Glu Lys Thr Val Pro Gly Ile Ile
        195                 200                 205

Asp Lys Phe Gly Trp Cys Thr Trp Asp Ala Phe Tyr Leu Asn Val His
    210                 215                 220

Pro Glu Gly Val Arg Glu Gly Ile Lys Gly Leu Val Glu Gly Gly Cys
225                 230                 235                 240

Pro Pro Gly Leu Val Leu Ile Asp Asp Gly Trp Gln Thr Phe Cys Arg
                245                 250                 255

Asp Asp Glu Thr Val Ser Asp Gly Gly Ser Leu Asn Cys Ser Val Pro
            260                 265                 270

Gly Glu Gln Met Leu Asn Arg Leu Ile Lys Phe Glu Glu Asn Gly Lys
```

```
              275                 280                 285
Phe Lys Glu Tyr Lys Cys Gly Arg Glu Gly Asn Lys Gly Met Gly Ala
290                 295                 300
Phe Val Arg Glu Leu Lys Glu Glu Phe Ser Gly Leu Glu Tyr Val Tyr
305                 310                 315                 320
Val Trp His Ala Phe Cys Gly Tyr Trp Gly Val Arg Pro Lys Val
                325                 330                 335
Pro Gly Met Pro Glu Ala Thr Val Pro Thr Lys Leu Ser Pro Gly
        340                 345                 350
Ala Gly Xaa Thr Met Thr Asp Gln Ala Val Val Lys Ile Met Glu Ile
        355                 360                 365
Gly Val Gly Leu Val Pro Pro His Arg Ala His Glu Leu Tyr Glu Gly
370                 375                 380
Leu His Ser His Leu Glu Ser Val Gly Ile Asp Gly Val Lys Ile Asp
385                 390                 395                 400
Val Thr His Ile Leu Glu Met Leu Ser Glu Glu Tyr Gly Gly Arg Val
                405                 410                 415
Glu Leu Ala Lys Ala Tyr Tyr Lys Ala Leu Thr Ala Ser Val Arg Lys
        420                 425                 430
His Phe Lys Gly Asn Gly Val Ile Ser Ser Met Gln Gln Cys Asn Asp
        435                 440                 445
Phe Met Phe Leu Gly Thr Glu Thr Ile Ser Leu Gly Arg Val Asp Ser
450                 455                 460
Phe His Lys Cys Glu Leu Trp Tyr Ile His Ala Gly Asp Asp Phe Trp
465                 470                 475                 480
Cys Thr Asp Pro Ala Gly Asp Pro Asn Gly Thr Tyr Trp Leu Gln Gly
                485                 490                 495
Cys His Met Val His Cys Ala Tyr Asn Ser Leu Trp Met Gly Asn Phe
        500                 505                 510
Ile His Pro Asp Trp Asp Met Phe Gln Ser Asp His Ala Cys Ala Glu
        515                 520                 525
Phe His Ala Ala Ser Arg Ala Ile Ser Gly Gly Pro Ile Tyr Val Ser
530                 535                 540
Asp Ser Val Gly Lys His Asn Phe Lys Leu Leu Lys Lys Leu Val Leu
545                 550                 555                 560
Pro Asp Gly Ser Ile Leu Arg Cys Gln His Tyr Ala Leu Pro Thr Arg
                565                 570                 575
Asp Cys Leu Phe Val Asp Pro Leu His Asp Gly Lys Thr Met Leu Lys
        580                 585                 590
Ile Trp Asn Leu Asn Lys Cys Ser Gly Val Leu Gly Leu Phe Asn Cys
        595                 600                 605
Gln Gly Gly Gly Trp Cys Pro Val Thr Arg Arg Asn Lys Ser Ser Ser
610                 615                 620
Asp Tyr Ser His Ser Val Thr Cys Phe Ala Ser Pro Gln Asp Ile Glu
625                 630                 635                 640
Trp Gly Lys Gly Lys His Pro Val Cys Ile Lys Gly Val Asp Val Phe
                645                 650                 655
Ala Val Tyr Met Phe Lys Asp Asp Lys Leu Lys Leu Leu Lys Tyr Thr
        660                 665                 670
Glu Ser Val Glu Val Ser Leu Glu Pro Phe Ser Cys Glu Leu Leu Thr
        675                 680                 685
Val Ser Pro Val Val Ile Leu Pro Arg Lys Ser Ile Gln Phe Ala Pro
690                 695                 700
```

```
Ile Gly Leu Val Asn Met Leu Asn Ser Gly Gly Ser Ile Met Ser Leu
705                 710                 715                 720

Glu Phe Asp Gln Gln Glu Asn Leu Ala Arg Ile Gly Val Arg Gly His
            725                 730                 735

Gly Glu Met Arg Val Phe Ala Ser Glu Lys Pro Glu Ser Val Lys Ile
        740                 745                 750

Asp Gly Glu Ser Val Glu Phe Asp Tyr Val Asp Arg Thr Val Arg Leu
    755                 760                 765

Gln Val Ser Trp Pro Cys Ser Ser Arg Leu Ser Val Val Glu Tyr Leu
770                 775                 780

Phe
785

<210> SEQ ID NO 7
<211> LENGTH: 34
<212> TYPE: DNA
<213> ORGANISM: Glycine max

<400> SEQUENCE: 7
gcgggcaggg cggctggagc aggtgtatat gtgg                            34

<210> SEQ ID NO 8
<211> LENGTH: 26
<212> TYPE: DNA
<213> ORGANISM: Glycine max

<400> SEQUENCE: 8
gcgggctgga gcaggtgtat ttgcac                                    26

<210> SEQ ID NO 9
<211> LENGTH: 23
<212> TYPE: DNA
<213> ORGANISM: Glycine max

<400> SEQUENCE: 9
tgggtctgac cccaccccaa tac                                       23

<210> SEQ ID NO 10
<211> LENGTH: 20
<212> TYPE: DNA
<213> ORGANISM: Glycine max

<400> SEQUENCE: 10
ctagggccat ctctggtgga                                           20

<210> SEQ ID NO 11
<211> LENGTH: 20
<212> TYPE: DNA
<213> ORGANISM: Glycine max

<400> SEQUENCE: 11
cgtgtgggga gtgcatagtg                                           20

<210> SEQ ID NO 12
<211> LENGTH: 42
<212> TYPE: DNA
<213> ORGANISM: Glycine max

<400> SEQUENCE: 12
gcgggcaggg cggcatgggt ccaagctcga agaaagcgtc ac                  42

<210> SEQ ID NO 13
```

-continued

```
<211> LENGTH: 34
<212> TYPE: DNA
<213> ORGANISM: Glycine max

<400> SEQUENCE: 13
gcgggcatgg gtccaagctc gaagaaagcc tcag                              34

<210> SEQ ID NO 14
<211> LENGTH: 27
<212> TYPE: DNA
<213> ORGANISM: Glycine max

<400> SEQUENCE: 14
gagttgcaga ggctgaagcc cttcatg                                      27

<210> SEQ ID NO 15
<211> LENGTH: 20
<212> TYPE: DNA
<213> ORGANISM: Glycine max

<400> SEQUENCE: 15
cactggagtt cttggggtgt                                              20

<210> SEQ ID NO 16
<211> LENGTH: 20
<212> TYPE: DNA
<213> ORGANISM: Glycine max

<400> SEQUENCE: 16
gcttggctga aatacgaagc                                              20

<210> SEQ ID NO 17
<211> LENGTH: 24
<212> TYPE: DNA
<213> ORGANISM: Glycine max

<400> SEQUENCE: 17
ctgtaacaag atggatgcca ctac                                         24

<210> SEQ ID NO 18
<211> LENGTH: 20
<212> TYPE: DNA
<213> ORGANISM: Glycine max

<400> SEQUENCE: 18
cagtcaaggt tagtggacct                                              20
```